US007909888B2

(12) United States Patent
Hercouet et al.

(10) Patent No.: US 7,909,888 B2
(45) Date of Patent: Mar. 22, 2011

(54) PROCESS FOR DYEING OR LIGHTENING HUMAN KERATIN FIBERS USING AN ANHYDROUS COMPOSITION AND A MONOETHANOLAMINE/BASIC AMINO ACID MIXTURE, AND SUITABLE DEVICE THEREFOR

(75) Inventors: Leïla Hercouet, Neuilly Plaisance (FR); Alain Lagrange, Coupvray (FR); Marie Giafferi, Villemombie (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 12/642,624

(22) Filed: Dec. 18, 2009

(65) Prior Publication Data

US 2010/0175706 A1  Jul. 15, 2010

Related U.S. Application Data

(60) Provisional application No. 61/147,840, filed on Jan. 28, 2009, provisional application No. 61/155,632, filed on Feb. 26, 2009.

(30) Foreign Application Priority Data

Dec. 19, 2008  (FR) ...................................... 08 07294
Dec. 19, 2008  (FR) ...................................... 08 07307

(51) Int. Cl.
    *A61Q 5/10* (2006.01)
(52) U.S. Cl. ............. 8/405; 8/406; 8/407; 8/426; 8/431; 8/462; 8/602; 8/604; 8/111; 132/202; 132/208
(58) Field of Classification Search ............... 8/405, 406, 8/407, 426, 431, 462, 463, 602, 604, 111; 132/202, 208
    See application file for complete search history.

(56) References Cited

U.S. PATENT DOCUMENTS

| 3,100,739 | A | | 8/1963 | Kaiser et al. |
| 3,369,970 | A | | 2/1968 | McLaughlin et al. |
| 3,629,330 | A | | 12/1971 | Brody et al. |
| 3,861,868 | A | | 1/1975 | Milbrada |
| 4,138,478 | A | | 2/1979 | Reese et al. |
| 4,170,637 | A | | 10/1979 | Pum |
| 4,226,851 | A | | 10/1980 | Sompayrac |
| 4,357,141 | A | | 11/1982 | Grollier et al. |
| 4,366,099 | A | | 12/1982 | Gaetani et al. |
| 4,488,564 | A | | 12/1984 | Grollier et al. |
| 4,725,282 | A | | 2/1988 | Hoch et al. |
| 4,845,293 | A | | 7/1989 | Junino et al. |
| 5,021,066 | A | | 6/1991 | Aeby et al. |
| 5,259,849 | A | * | 11/1993 | Grollier et al. ................ 8/405 |
| 5,364,414 | A | | 11/1994 | Lang et al. |
| 5,817,155 | A | | 10/1998 | Yasuda et al. |
| 6,010,541 | A | | 1/2000 | De La Mettrie |
| 6,074,439 | A | | 6/2000 | De La Mettrie et al. |
| 6,129,770 | A | | 10/2000 | Deutz et al. |
| 6,156,713 | A | | 12/2000 | Chopra et al. |
| 6,165,444 | A | | 12/2000 | Dubief et al. |
| 6,190,421 | B1 | | 2/2001 | Rondeau et al. |
| 6,206,935 | B1 | | 3/2001 | Onitsuka et al. |
| 6,238,653 | B1 | | 5/2001 | Narasimhan et al. |
| 6,251,378 | B1 | | 6/2001 | Laurent et al. |
| 6,260,556 | B1 | | 7/2001 | Legrand et al. |
| 6,277,154 | B1 | | 8/2001 | Lorenz |
| 6,277,155 | B1 | | 8/2001 | De La Mettrie et al. |
| 6,365,136 | B1 | | 4/2002 | Lauscher et al. |
| 6,423,100 | B1 | | 7/2002 | Lang et al. |
| 6,447,552 | B1 | | 9/2002 | Golinski |
| 6,645,258 | B2 | | 11/2003 | Vidal et al. |
| 6,660,045 | B1 | | 12/2003 | Hoeffkes et al. |
| 6,695,887 | B2 | | 2/2004 | Cottard et al. |
| 6,800,098 | B1 | | 10/2004 | Allard et al. |
| 7,135,046 | B2 | | 11/2006 | Audousset |
| 7,153,331 | B2 | | 12/2006 | Desenne et al. |
| 7,217,298 | B2 | | 5/2007 | Legrand et al. |
| 7,285,137 | B2 | | 10/2007 | Vidal et al. |
| 7,442,215 | B2 | | 10/2008 | Audousset et al. |
| 7,458,993 | B2 | | 12/2008 | Cottard et al. |
| 7,494,513 | B2 | | 2/2009 | Kravtchenko et al. |
| 7,575,605 | B2 | | 8/2009 | Legrand |
| 7,651,533 | B2 | | 1/2010 | Legrand |
| 7,651,536 | B2 | | 1/2010 | Cottard et al. |
| 7,766,977 | B2 | | 8/2010 | Cottard et al. |
| 2003/0190297 | A1 | | 10/2003 | Narasimhan et al. |

(Continued)

FOREIGN PATENT DOCUMENTS

CA  1 268 421  5/1990

(Continued)

OTHER PUBLICATIONS

French Search Report for FR 08/07294, dated Aug. 19, 2009.

(Continued)

*Primary Examiner* — Eisa B Elhilo
(74) *Attorney, Agent, or Firm* — Finnegan, Henderson, Farabow, Garrett & Dunner

(57) ABSTRACT

Provided is a process for dyeing or lightening human keratin fibers, comprising applying to the keratin fibers: a) at least one anhydrous composition (A) comprising at least one fatty substance and at least one surfactant; b) at least one composition (B) comprising monoethanolamine and at least one basic amino acid; and c) at least one composition (C) comprising at least one oxidizing agent; provided that when the process is a dyeing process, the at least one anhydrous composition (A) is free from organic amines and the at least one composition (B) comprises at least one oxidation dye and/or at least one direct dye fiber. Also provided is a multi-compartment device comprising: a first compartment comprising at least one an anhydrous composition (A) comprising at least one fatty substance and at least one surfactant; a second compartment comprising at least composition (B) comprising monoethanolamine and at least one basic amino acid; and a third compartment comprising at least one composition (C) comprising at least one oxidizing agent.

24 Claims, No Drawings

U.S. PATENT DOCUMENTS

| | | |
|---|---|---|
| 2003/0226217 A1 | 12/2003 | Bowes et al. |
| 2004/0103488 A1 | 6/2004 | Yamashita et al. |
| 2004/0105830 A1 | 6/2004 | Boswell et al. |
| 2004/0181883 A1 | 9/2004 | Legrand et al. |
| 2004/0226110 A1 | 11/2004 | LeGrand |
| 2004/0234700 A1 | 11/2004 | Legrand et al. |
| 2005/0129652 A1 | 6/2005 | Keller et al. |
| 2005/0165705 A1 | 7/2005 | Lauper et al. |
| 2005/0196367 A1 | 9/2005 | Ohta et al. |
| 2006/0042023 A1 | 3/2006 | Machida |
| 2006/0075580 A1 | 4/2006 | Chan et al. |
| 2006/0137111 A1 | 6/2006 | Au et al. |
| 2006/0242773 A1 | 11/2006 | Kravtchenko et al. |
| 2006/0260071 A1 | 11/2006 | Legrand |
| 2006/0265817 A1 | 11/2006 | Legrand |
| 2007/0006397 A1 | 1/2007 | Schmenger et al. |
| 2007/0033743 A1 | 2/2007 | Kravtchenko |
| 2007/0104672 A1 | 5/2007 | Decoster et al. |
| 2007/0169285 A1 | 7/2007 | Narasimhan et al. |
| 2007/0275927 A1 | 11/2007 | Philippe |
| 2007/0277331 A1 | 12/2007 | Goldstein et al. |
| 2008/0016627 A1 | 1/2008 | Cottard et al. |
| 2008/0071092 A1 | 3/2008 | Vidal et al. |
| 2008/0229512 A1 | 9/2008 | Syed et al. |
| 2008/0256724 A1 | 10/2008 | Bolton et al. |
| 2009/0007347 A1 | 1/2009 | Cottard et al. |
| 2009/0060855 A1 | 3/2009 | Boche et al. |
| 2009/0151086 A1 | 6/2009 | Brun |
| 2009/0151087 A1 | 6/2009 | Mario et al. |
| 2009/0158533 A1 | 6/2009 | Hercouet |
| 2009/0162309 A1 | 6/2009 | Hercouet et al. |
| 2009/0191142 A1 | 7/2009 | Hercouet et al. |

FOREIGN PATENT DOCUMENTS

| | | |
|---|---|---|
| CA | 2 573 567 | 3/2006 |
| CH | 507 713 | 7/1971 |
| DE | 20 05 076 | 8/1970 |
| DE | 38 14 356 | 9/1988 |
| DE | 38 14 685 | 9/1988 |
| DE | 43 09 509 | 9/1994 |
| DE | 195 27 121 | 1/1997 |
| DE | 197 23 538 | 9/1998 |
| DE | 197 12 980 | 10/1998 |
| DE | 197 54 281 | 6/1999 |
| DE | 198 15 338 | 9/1999 |
| DE | 100 08 640 | 8/2000 |
| DE | 199 09 661 | 9/2000 |
| DE | 199 62 869 | 6/2001 |
| DE | 100 28 723 | 12/2001 |
| DE | 100 56 266 | 5/2002 |
| DE | 101 48 571 | 4/2003 |
| DE | 101 48 671 | 4/2003 |
| DE | 20 2005 008 307 | 7/2005 |
| DE | 10 2005 011 459 | 9/2006 |
| DE | 10 2005 032 798 | 1/2007 |
| DE | 10 2006 012 575 | 2/2007 |
| DE | 10 2005 059 647 | 6/2007 |
| DE | 10 2006 020 050 | 10/2007 |
| DE | 10 2006 061 830 | 6/2008 |
| EP | 0 166 100 | 1/1986 |
| EP | 0 424 261 | 4/1991 |
| EP | 0 890 355 | 1/1999 |
| EP | 1 023 891 | 8/2000 |
| EP | 1 142 563 | 10/2001 |
| EP | 1 166 749 | 1/2002 |
| EP | 1 219 285 | 7/2002 |
| EP | 1 291 006 | 3/2003 |
| EP | 1 314 418 | 5/2003 |
| EP | 1 321 132 | 6/2003 |
| EP | 1 374 842 | 1/2004 |
| EP | 1 430 873 | 6/2004 |
| EP | 1 438 951 | 7/2004 |
| EP | 1 449 512 | 8/2004 |
| EP | 1 486 195 | 12/2004 |
| EP | 1 488 781 | 12/2004 |
| EP | 1 550 656 | 7/2005 |
| EP | 1 568 354 | 8/2005 |
| EP | 1 570 833 | 9/2005 |
| EP | 1 598 052 | 11/2005 |
| EP | 1 707 184 | 10/2006 |
| EP | 1 716 839 | 11/2006 |
| EP | 1 716 840 | 11/2006 |
| EP | 1 733 759 | 12/2006 |
| EP | 1 762 222 | 3/2007 |
| EP | 1 792 602 | 6/2007 |
| EP | 1 813 254 | 8/2007 |
| EP | 1 862 198 | 12/2007 |
| EP | 1 870 085 | 12/2007 |
| EP | 1 902 703 | 3/2008 |
| EP | 1 927 377 | 6/2008 |
| EP | 1 944 009 | 7/2008 |
| EP | 2 005 939 | 12/2008 |
| EP | 2 011 474 | 1/2009 |
| EP | 2 018 848 | 1/2009 |
| EP | 2 072 034 | 6/2009 |
| EP | 2 072 035 | 6/2009 |
| EP | 2 072 036 | 6/2009 |
| FR | 1 517 715 | 3/1968 |
| FR | 2 132 214 | 11/1972 |
| FR | 2 402 446 | 4/1979 |
| FR | 2 496 458 | 6/1982 |
| FR | 2 616 324 | 12/1988 |
| FR | 2 769 835 | 4/1999 |
| FR | 2 779 949 | 12/1999 |
| FR | 2 803 196 | 7/2001 |
| FR | 2 842 101 | 1/2004 |
| FR | 2 870 724 | 12/2005 |
| FR | 2 874 323 | 2/2006 |
| FR | 2 892 623 | 5/2007 |
| FR | 2 910 309 | 6/2008 |
| FR | 2 911 499 | 7/2008 |
| FR | 2 912 903 | 8/2008 |
| FR | 2 912 904 | 8/2008 |
| FR | 2 912 906 | 8/2008 |
| FR | 2 915 886 | 11/2008 |
| FR | 2 919 499 | 2/2009 |
| FR | 2 925 304 | 6/2009 |
| FR | 2 925 307 | 6/2009 |
| FR | 2 925 308 | 6/2009 |
| FR | 2 925 309 | 6/2009 |
| FR | 2 925 311 | 6/2009 |
| GB | 1 288 128 | 9/1972 |
| GB | 1 554 331 | 10/1979 |
| GB | 2 065 177 | 6/1981 |
| GB | 2 142 348 | 1/1985 |
| GB | 2 170 830 | 8/1986 |
| GB | 2 188 948 | 10/1987 |
| GB | 2 217 735 | 11/1989 |
| JP | 58-035106 | 3/1983 |
| JP | 59-106413 | 6/1984 |
| JP | 1-165514 | 6/1989 |
| JP | 10-101537 | 4/1998 |
| JP | 2001-233748 | 8/2001 |
| JP | 2001-302471 | 10/2001 |
| JP | 2003-095984 | 4/2003 |
| JP | 2003-238370 | 8/2003 |
| JP | 2004-262886 | 9/2004 |
| JP | 2006-282524 | 10/2006 |
| JP | 2008-74705 | 4/2008 |
| WO | WO 91/11985 | 8/1991 |
| WO | WO 97/01323 | 1/1997 |
| WO | WO 97/04739 | 2/1997 |
| WO | WO 97/12587 | 4/1997 |
| WO | WO 98/03150 | 1/1998 |
| WO | WO 01/28508 | 4/2001 |
| WO | WO 01/41723 | 6/2001 |
| WO | WO 01/43709 | 6/2001 |
| WO | WO 01/60327 | 8/2001 |
| WO | WO 02/089748 | 11/2002 |
| WO | WO 03/053329 | 7/2003 |
| WO | WO 03/084495 | 10/2003 |
| WO | WO 2005/025525 | 3/2005 |
| WO | WO 2005/055966 | 6/2005 |
| WO | WO 2006/026851 | 3/2006 |
| WO | WO 2007/006418 | 1/2007 |
| WO | WO 2007/096027 | 8/2007 |

| | | |
|---|---|---|
| WO | WO 2008/021641 | 2/2008 |
| WO | WO 2008/096497 | 8/2008 |
| WO | WO 2009/080667 | 7/2009 |
| WO | WO 2009/080668 | 7/2009 |
| WO | WO 2009/080669 | 7/2009 |
| WO | WO 2009/080670 | 7/2009 |

OTHER PUBLICATIONS

French Search Report for FR 08/07307, dated Aug. 24, 2009.
English language Abstract of EP 1 568 354, dated Aug. 31, 2005.
English language Abstract of FR 2 925 308, dated Jun. 26, 2009.
English language Abstract of FR 2 925 309, dated Jun. 26, 2009.
English language Abstract of JP 59-106413, dated Jun. 20, 1984.
English language Abstract of JP 2004-262886, dated Sep. 24, 2004.
English language Abstract of WO 97/04739, dated Feb. 13, 1997.
English language Abstract of WO 2007/096027, dated Aug. 30, 2007.
Copending U.S. Appl. No. 12/339,753, filed Dec. 19, 2008.
Copending U.S. Appl. No. 12/339,781, filed Dec. 19, 2008.
Copending U.S. Appl. No. 12/339,820, filed Dec. 19, 2008.
Copending U.S. Appl. No. 12/642,412, filed Dec. 18, 2009.
Copending U.S. Appl. No. 12/642,451, filed Dec. 18, 2009.
Copending U.S. Appl. No. 12/642,468, filed Dec. 18, 2009.
Copending U.S. Appl. No. 12/642,473, filed Dec. 18, 2009.
Copending U.S. Appl. No. 12/642,480, filed Dec. 18, 2009.
Copending U.S. Appl. No. 12/642,489, filed Dec. 18, 2009.
Copending U.S. Appl. No. 12/642,492, filed Dec. 18, 2009.
Copending U.S. Appl. No. 12/642,506, filed Dec. 18, 2009.
Copending U.S. Appl. No. 12/642,513, filed Dec. 18, 2009.
Copending U.S. Appl. No. 12/642,531, filed Dec. 18, 2009.
Copending U.S. Appl. No. 12/642,536, filed Dec. 18, 2009.
Copending U.S. Appl. No. 12/642,543, filed Dec. 18, 2009.
Copending U.S. Appl. No. 12/642,551, filed Dec. 18, 2009.
Copending U.S. Appl. No. 12/642,555, filed Dec. 18, 2009.
Copending U.S. Appl. No. 12/642,568, filed Dec. 18, 2009.
Copending U.S. Appl. No. 12/642,575, filed Dec. 18, 2009.
Copending U.S. Appl. No. 12/642,583, filed Dec. 18, 2009.
Copending U.S. Appl. No. 12/642,592, filed Dec. 18, 2009.
Copending U.S. Appl. No. 12/642,593, filed Dec. 18, 2009.
Copending U.S. Appl. No. 12/642,599, filed Dec. 18, 2009.
Copending U.S. Appl. No. 12/642,637, filed Dec. 18, 2009.
Copending U.S. Appl. No. 12/809,140, filed Jun. 18, 2010.
English language Abstract of DE 10 2005 011 459, dated Sep. 14, 2006.
English language Abstract of DE 10 2005 032 798, dated Jan. 25, 2007.
English language Abstract of DE 10 2005 059 647, dated Jun. 14, 2007.
English language Abstract of DE 10 2006 012 575, dated Feb. 8, 2007.
English language Abstract of DE 10 2006 020 050, dated Oct. 31, 2007.
English language Abstract of DE 10 2006 061 830, dated Jun. 26, 2008.
English language abstract of DE 100 28 723, dated Dec. 10, 2001.
English language Abstract of DE 100 56 266, dated May 23, 2002.
English language Abstract of DE 101 48 571, dated Apr. 24, 2003.
English language Abstract of DE 101 48 671, dated Apr. 10, 2003.
English language Abstract of DE 195 27 121, dated Jan. 30, 1997.
English language Abstract of DE 197 12 980, dated Oct. 1, 1998.
English language Abstract of DE 197 23 538, dated Sep. 17, 1998.
English language Abstract of DE 199 62 869, dated Jun. 28, 2001.
English language Abstract of DE 38 14 356, dated Sep. 8, 1988.
English language Abstract of DE 43 09 509, dated Sep. 19, 1994.
English language Abstract of EP 1 166 749, dated Jan. 22, 2002.
English language Abstract of EP 1 321 132, dated Jun. 25, 2003.
English language Abstract of EP 1 862 198, dated Dec. 5, 2007.
English language Abstract of EP 2 005 939, dated Dec. 24, 2008.
English language Abstract of EP 2 018 848, dated Jan. 28, 2009.
English language Abstract of FR 2 616 324, dated Dec. 16, 1988.
English language Abstract of FR 2 779 949, dated Dec. 24, 1999.
English language Abstract of FR 2 842 101, dated Jan. 16, 2004.
English language Abstract of FR 2 870 724, dated Dec. 2, 2005.
English language Abstract of FR 2 910 309, dated Jun. 27, 2008.
English language Abstract of FR 2 911 499, dated Jul. 25, 2008.
English language Abstract of FR 2 912 903, dated Aug. 29, 2008.
English language Abstract of FR 2 912 904, dated Aug. 29, 2008.
English language Abstract of FR 2 912 906, dated Aug. 29, 2008.
English language Abstract of FR 2 915 886, dated Nov. 14, 2008.
English language Abstract of FR 2 919 499, dated Feb. 6, 2009.
English language Abstract of FR 2 925 304, dated Jun. 26, 2009.
English language Abstract of JP 1-165514, dated Jun. 29, 1989.
English language Abstract of JP 2001-233748, dated Aug. 28, 2001.
English language Abstract of JP 2001-302471, dated Oct. 31, 2001.
English language Abstract of JP 2003-095984, dated Apr. 3, 2003.
English language Abstract of JP 2003-238370, dated Aug. 27, 2003.
English language Abstract of JP 2006-282524, dated Oct. 19, 2006.
English language Abstract of JP 2008-074705, dated Apr. 3, 2008.
English language Abstract of JP 58-035106, dated Mar. 1, 1983.
English language Abstract of WO 91/11985, dated Aug. 22, 1991.
English language Abstract of WO 2007/06418, dated Jan. 18, 2007.
English language Abstract of WO 2008/096497, dated Aug. 14, 2008.
European Search Report for EP 08 17 2444, dated Apr. 13, 2009.
European Search Report for EP 08 17 2449, dated Apr. 13, 2009.
European Search Report for EP 08 17 2454, dated Apr. 3, 2009.
European Search Report for EP 09 17 9779, dated May 5, 2010.
European Search Report for EP 09 17 9789, dated Feb. 19, 2010.
European Search Report for EP 09 17 9844, dated Apr. 22, 2010.
European Search Report for EP 09 17 9884, dated Feb. 24, 2010.
European Search Report for EP 09 17 9885, dated Feb. 25, 2010.
European Search Report for EP 09 17 9887, dated Feb. 25, 2010.
European Search Report for EP 09 17 9888, dated Mar. 24, 2010.
European Search Report for EP 09 17 9892, dated Apr. 8, 2010.
European Search Report for EP 09 17 9895, dated Feb. 23, 2010.
European Search Report for EP 09 17 9899, dated Mar. 17, 2010.
European Search Report for EP 09 17 9911, dated Apr. 26, 2010.
European Search Report for EP 09 17 9914, dated Mar. 25, 2010.
European Search Report for EP 09 17 9992, dated Mar. 24, 2010.
European Search Report for EP 09 18 0003, dated Feb. 24, 2010.
French Search Report for FR 07/60273, dated Aug. 20, 2008.
French Search Report for FR 07/60274, dated Aug. 20, 2008.
French Search Report for FR 07/60277, dated Aug. 20, 2008.
French Search Report for FR 07/60278, dated Aug. 20, 2008.
French Search Report for FR 08/07283, dated Sep. 30, 2009.
French Search Report for FR 08/07285, dated Sep. 28, 2009.
French Search Report for FR 08/07286, dated Sep. 24, 2009.
French Search Report for FR 08/07287, dated Oct. 13, 2009.
French Search Report for FR 08/07288, dated Nov. 4, 2009.
French Search Report for FR 08/07290, dated Oct. 14, 2009.
French Search Report for FR 08/07291, dated Oct. 19, 2009.
French Search Report for FR 08/07292, dated Aug. 25, 2009.
French Search Report for FR 08/07298, dated Nov. 2, 2009.
French Search Report for FR 08/07304, dated Oct. 1, 2009.
French Search Report for FR 08/07306, dated Aug. 13, 2009.
French Search Report for FR 08/07309, dated Aug. 3, 2009.
French Search Report for FR 08/07310, dated Oct. 2, 2009.
French Search Report for FR 08/07312, dated Oct. 1, 2009.
French Search Report for FR 08/07313, dated Aug. 26, 2009.
French Search Report for FR 08/07314, dated Aug. 27, 2009.
French Search Report for FR 08/07315, dated Nov. 11, 2009.
French Search Report for FR 08/07316, dated Nov. 18, 2009.
French Search Report for FR 08/07319, dated Aug. 3, 2009.
French Search Report for FR 08/07320, dated Sep. 15, 2009.
French Search Report for FR 08/07321, dated Aug. 5, 2009.
French Search Report for FR 08/07322, dated Sep. 24, 2009.
French Search Report for FR 08/07323, dated Sep. 24, 2009.
French Search Report for FR 08/58838, dated Sep. 3, 2009.
French Search Report for FR 08/58840, dated Sep. 30, 2009.
French Search Report for FR 08/58880, dated Sep. 18, 2009.
French Search Report for FR 08/58881, dated Sep. 29, 2009.
French Search Report for FR 08/58886, dated Nov. 3, 2009.
French Search Report for FR 08/58888, dated Nov. 3, 2009.
French Search Report for FR 08/58889, dated Sep. 30, 2009.
French Search Report for FR 08/58890, dated Sep. 21, 2009.
French Search Report for FR 08/58891, dated Aug. 24, 2009.
French Search Report for FR 08/58892, dated Sep. 24, 2009.
French Search Report for FR 09/51367, dated Jan. 29, 2010.

French Search Report for FR 09/54264, dated Mar. 5, 2010.
French Search Report for FR 09/56389, dated Jun. 14, 2010.
French Search Report for FR 09/57176, dated Jun. 17, 2010.
International Search Report for PCT/FR2009/052617, dated Mar. 30, 2010.
Notice of Allowance mailed Aug. 10, 2010, in U.S. Appl. No. 12/339,820.
Notice of Allowance mailed Aug. 26, 2010, in U.S. Appl. No. 12/642,637.
Notice of Allowance mailed Aug. 27, 2010, in U.S. Appl. No. 12/642,513.
Notice of Allowance mailed in co-pending U.S. Appl. No. 12/339,753, dated Jul. 9, 2010.
Notice of Allowance mailed Jun. 11, 2010, in U.S. Appl. No. 12/642,489.
Notice of Allowance mailed Oct. 26, 2010, in U.S. Appl. No. 12/339,753.
Notice of Allowance mailed Sep. 16, 2010, in U.S. Appl. No. 12/642,480.
Notice of Allowance mailed Sep. 16, 2010, in U.S. Appl. No. 12/642,555.
Notice of Allowance mailed Sep. 21, 2010, in U.S. Appl. No. 12/642,489.
Notice of Allowance mailed Sep. 22, 2010, in U.S. Appl. No. 12/642,551.
Notice of Allowance mailed Sep. 23, 2010, in U.S. Appl. No. 12/642,536.
Notice of Allowance mailed Sep. 7, 2010, in U.S. Appl. No. 12/642,599.
Notice of Allowance mailed Sep. 8, 2010, in U.S. Appl. No. 12/642,543.
Notice of Allowance mailed Sep. 9, 2010, in U.S. Appl. No. 12/642,531.
Office Action mailed Aug. 11, 2010, in co-pending U.S. Appl. No. 12/642,593.
Office Action mailed Aug. 26, 2010, in co-pending U.S. Appl. No. 12/642,473.
Office Action mailed Feb. 1, 2010, in co-pending U.S. Appl. No. 12/339,753.
Office Action mailed Mar. 15, 2010, in co-pending U.S. Appl. No. 12/339,820.
Office Action mailed Sep. 17, 2010, in co-pending U.S. Appl. No. 12/642,506.
Office Action mailed Sep. 21, 2010, in co-pending U.S. Appl. No. 12/642,468.
Office Action mailed Sep. 22, 2010, in co-pending U.S. Appl. No. 12/642,492.
Office Action mailed Sep. 3, 2010, in co-pending U.S. Appl. No. 12/642,451.
STIC Search Report for U.S. Appl. No. 12/339,820, dated Jan. 21, 2010.
STIC Search Report for U.S. Appl. No. 12/642,492, dated Jul. 14, 2010.

* cited by examiner

PROCESS FOR DYEING OR LIGHTENING HUMAN KERATIN FIBERS USING AN ANHYDROUS COMPOSITION AND A MONOETHANOLAMINE/BASIC AMINO ACID MIXTURE, AND SUITABLE DEVICE THEREFOR

This application claims benefit of U.S. Provisional Application Nos. 61/147,840, filed Jan. 28, 2009, and 61/155,632, filed Feb. 26, 2009. This application also claims benefit of priority under 35 U.S.C. §119 to French Patent Application Nos. 0807294 and 0807307, filed Dec. 19, 2009.

Provided herein is a process for dyeing or lightening human keratin fibers using at least one anhydrous composition (A) comprising at least one fatty substance and at least one surfactant; at least one composition (B) comprising monoethanolamine and at least one basic amino acid; and at least one composition (C) comprising at least one oxidizing agent; provided that when the process is a dyeing process, the at least one anhydrous composition (A) is free from organic amines and the at least one composition (B) comprises at least one oxidation dye and/or at least one direct dye.

Also provided is a multi-compartment device, at least one of which comprises the abovementioned anhydrous cosmetic composition (A), another comprises the abovementioned composition (B) and a final one comprises the abovementioned oxidizing composition (C).

Among the methods for dyeing human keratin fibers, such as the hair, mention may be made of oxidation dyeing or permanent dyeing. For example, this dyeing method uses at least one oxidation dye precursor, usually at least one oxidation base optionally combined with at least one coupler.

In general, the at least one oxidation base may be chosen from ortho- or para-phenylenediamines, ortho- or para-aminophenols and heterocyclic compounds. The at least one oxidation base may be a colorless or weakly colored compound, which, when combined with oxidizing products, can give access to colored species via a process of oxidative condensation.

The shades obtained with the at least one oxidation base may be varied by combining it with at least one coupler, the at least one coupler being chosen for example from aromatic meta-diamines, meta-aminophenols, meta-diphenols and certain heterocyclic compounds, such as indole compounds.

The variety of molecules used as oxidation bases and couplers may allow a wide range of colors to be obtained.

Direct dyeing or semi-permanent dyeing is also known. The process conventionally used in direct dyeing consists in applying to the keratin fibers at least one direct dye, which is a colored and coloring molecule that has affinity for the fibers, in leaving it on for a time to allow the molecules to penetrate, by diffusion, into the fiber, and then in rinsing it off.

The at least one direct dye generally used may be chosen from nitrobenzene, anthraquinone, nitropyridine, azo, methine, azomethine, xanthene, acridine, azine and triarylmethane direct dyes.

This type of process may not require the use of an oxidizing agent to develop the coloration. However, at least one oxidizing agent may be used to obtain, along with the coloration, a lightening effect. Such a process is then referred to as "direct dyeing" or "semi-permanent dyeing under lightening conditions."

Processes of permanent or semi-permanent dyeing under lightening conditions thus may consist in using, along with the dye composition, an aqueous composition comprising at least one oxidizing agent, under alkaline pH conditions for example. The role of the at least one oxidizing agent is to degrade the melanin of the hair, which, depending on the nature of the oxidizing agent present, may lead to more or less pronounced lightening of the fibers. Thus, for relatively weak lightening, the oxidizing agent is often hydrogen peroxide. When greater lightening is desired, peroxygenated salts, for instance persulfates, may be used in the presence of hydrogen peroxide.

Processes for lightening human keratin fibers may consist in using an aqueous composition comprising at least one oxidizing agent, under alkaline pH conditions for instance. The at least one oxidizing agent has the role of degrading the melanin of the hair, which, depending on the nature of the oxidizing agent present, may lead to a more or less pronounced lightening of the fibers. Thus, for relatively weak lightening, the oxidizing agent is often hydrogen peroxide. When greater lightening is sought, use may be made of peroxygenated salts, for instance persulfates, in the presence of hydrogen peroxide.

These processes for dyeing or lightening keratin fibers may be performed under alkaline conditions, and an alkaline agent commonly used is aqueous ammonia. Aqueous ammonia may allow the pH of the composition to be adjusted to an alkaline pH to enable activation of the oxidizing agent. However, this agent may cause swelling of the keratin fiber, with opening of the scales, which promotes the penetration of the oxidizing agent, and also of the dyes, for example the oxidation dyes in the case of dyeing processes, into the fiber, and thus may increase the efficacy of the dyeing reaction.

However, aqueous ammonia is volatile, which users find disagreeable due to the characteristic strong, rather unpleasant odor of ammonia that is given off during the process.

Furthermore, the amount of ammonia given off requires the use of higher contents than necessary in order to compensate for the loss. Thus the user may be inconvenienced by the odor and confronted with greater risks of intolerance, for instance irritation of the scalp (stinging).

Replacing all or some of the aqueous ammonia with one or more other standard alkaline agents may not lead to compositions that are as efficient as those based on aqueous ammonia, for example because standard alkaline agents may not afford sufficient lightening of pigmented fibers in the presence of the oxidizing agent.

Provided are processes for dyeing or lightening human keratin fibers, performed in the presence of at least one oxidizing agent, which may not have the drawbacks of those performed with the existing compositions, these drawbacks being caused by the presence of large amounts of ammonia, but which may remain at least as effective in terms of the dyeing power obtained, the chromaticity, the uniformity of dyeing along the fiber, for dyeing processes, and in terms of the lightening and the uniformity of this lightening, for lightening processes.

Provided is a process for dyeing or lightening human keratin fibers in the presence of at least one oxidizing agent, comprising applying to the keratin fibers a cosmetic composition comprising:

a) at least one anhydrous composition (A) comprising at least one fatty substance and at least one surfactant;

b) at least one composition (B) comprising monoethanolamine and at least one basic amino acid; and c) at least one composition (C) comprising at least one oxidizing agent;

provided that when the process is a dyeing process, the at least one anhydrous composition (A) is free from organic amines and the at least one composition (B) comprises at least one oxidation dye and/or at least one direct dye.

Provided also is a multi-compartment device comprising,
a first compartment comprising at least one anhydrous composition (A) comprising at least one fatty substance and at least one surfactant;
a second compartment comprising at least composition (B) comprising monoethanolamine and at least one basic amino acid; and
a third compartment comprising at least one composition (C) comprising at least one oxidizing agent.

In some embodiments of this multi-compartment device, the at least one anhydrous composition (A) is free from organic amine and the at least one composition (B) comprises at least one oxidation dye and/or at least one direct dye.

Other characteristics and benefits of the process described herein may emerge on reading the description and the examples that follow.

In the text herein, unless otherwise indicated, the limits of a range of values are included in that range.

The human keratin fibers treated via the process described herein may for example be hair.

The at least one anhydrous cosmetic composition (A) for example, has a water content ranging from 0 to less than 5% by weight, for example less than 2% by weight, such as less than 1% by weight, relative to the weight of the at least one anhydrous composition (A). The water may for example be bound water, such as the water of crystallization of salts or traces of water absorbed by the starting materials used in the preparation of the compositions described herein.

In addition, when the process is a lightening process, then the composition used does not comprise any direct dye or oxidation dye precursor (bases and couplers) usually used for the dyeing of human keratin fibers, or else, if it does comprise any, the direct dye and/or oxidation dye precursor are present in a total amount not exceeding 0.005% by weight relative to the weight of the at least one anhydrous composition (A) and of the at least one aqueous composition (C), comprising the at least one oxidizing agent. For example, at such a content, only the composition would possibly be dyed, i.e. no dyeing effect would be observed on the keratin fibers.

In some embodiments, the lightening process may be performed without at least one oxidation base, at least one coupler or at least one direct dye.

When the process is a dyeing process, in some embodiments, then the at least one anhydrous composition (A) is free from organic amines; for example, the at least one anhydrous composition (A) is free from organic amines with a pith at 25° C. of less than 12 (this value corresponds to the function of highest basicity).

As has been mentioned, the at least one anhydrous cosmetic composition (A) comprises at least one fatty substance.

As used herein, the term "fatty substance" means an organic compound that is insoluble in water at ordinary temperature (25° C.) and at atmospheric pressure (760 mmHg) (solubility of less than 5%, for example 1%, such as 0.1%). In some embodiments, the at least one fatty substance may present in its structure at least one hydrocarbon-based chain having at least 6 carbon atoms or a sequence of at least two siloxane groups. In addition, in some embodiments, the at least one fatty substance may be generally soluble in organic solvents under the same temperature and pressure conditions, for instance chloroform, ethanol, benzene, liquid petroleum jelly, or decamethylcyclopentasiloxane.

According to the process described herein, the at least one fatty substance may be chosen from compounds that are liquid or pasty at room temperature and at atmospheric pressure.

In some embodiments, the at least one fatty substance may be chosen from $C_6$-$C_{16}$ lower alkanes, non-silicone oils of animal, plant, mineral or synthetic origin, fatty alcohols, fatty acids, esters of a fatty acid and/or of a fatty alcohol, non-silicone waxes, and silicones.

In some embodiments, the fatty alcohols, fatty esters and fatty acids may for example contain at least one linear or branched, saturated or unsaturated hydrocarbon-based group having 6 to 30 carbon atoms, which is optionally substituted, for example with at least one hydroxyl group (such as 1 to 4). If they are unsaturated, in some embodiments, these compounds may comprise one to three conjugated or non-conjugated carbon-carbon double bonds.

As regards the $C_6$-$C_{16}$ lower alkanes, in some embodiments, they may be linear or branched, and possibly cyclic. Non-limiting examples that may be mentioned include hexane, undecane, dodecane, tridecane, and isoparaffins such as isohexadecane and isodecane.

As oils of animal, plant, mineral or synthetic origin that may be used in the process described herein, non-limiting examples that may be mentioned include:

hydrocarbon-based oils of animal origin, such as perhydrosqualene;

triglyceride oils of plant or synthetic origin, such as liquid fatty acid triglycerides having from 6 to 30 carbon atoms, for instance heptanoic or octanoic acid triglycerides, or alternatively, for example, sunflower oil, corn oil, soybean oil, marrow oil, grapeseed oil, sesameseed oil, hazelnut oil, apricot oil, macadamia oil, arara oil, sunflower oil, castor oil, avocado oil, caprylic/capric acid triglycerides, for instance those sold by the company Stéarineries Dubois or those sold under the names Miglyol® 810, 812 and 818 by the company Dynamit Nobel, jojoba oil and shea butter oil;

linear or branched hydrocarbons of mineral or synthetic origin, of more than 16 carbon atoms, such as volatile or non-volatile liquid paraffins, and the derivatives thereof, petroleum jelly, liquid petroleum jelly, polydecenes, hydrogenated polyisobutenes such as Parleam®; for example liquid paraffins, petroleum jelly, liquid petroleum jelly, polydecenes and hydrogenated polyisobutenes such as Parleam;

fluoro oils, for instance perfluoromethylcyclopentane and perfluoro-1,3-dimethylcyclohexane, sold under the names Flutec® PC1 and Flutec® PC3 by the company BNFL Fluorochemicals; perfluoro-1,2-dimethylcyclobutane; perfluoroalkanes such as dodecafluoropentane and tetradecafluorohexane, sold under the names PF 5050® and PF 5060® by the company 3M, or bromoperfluorooctyl sold under the name Foralkyl® by the company Atochem; nonafluoromethoxybutane and nonafluoroethoxyisobutane; perfluoromorpholine derivatives such as 4-trifluoromethyl perfluoromorpholine sold under the name PF 5052® by the company 3M.

In some embodiments, the fatty alcohols that may be used in the process described herein may for example be chosen from saturated or unsaturated, linear or branched alcohols having from 8 to 30 carbon atoms. Non-limiting examples that may be mentioned include cetyl alcohol, stearyl alcohol and the mixture thereof (cetylstearyl alcohol), octyldodecanol, 2-butyloctanol, 2-hexyldecanol, 2-undecylpentadecanol, oleyl alcohol or linoleyl alcohol.

The fatty acids that may be used in the process described herein may be chosen from saturated or unsaturated carboxylic acids having from 6 to 30 carbon atoms, such as from 9 to 30 carbon atoms. They for example, in some embodiments, may be chosen from myristic acid, palmitic acid, stearic acid, behenic acid, oleic acid, linoleic acid, linolenic acid and isostearic acid.

As regards the esters of a fatty acid and/or of a fatty alcohol, for example different from the triglycerides mentioned above; non-limiting mention may be made for instance of esters of saturated or unsaturated, linear or branched $C_1$-$C_{26}$ aliphatic mono- or polyacids and of saturated or unsaturated, linear or branched $C_1$-$C_{26}$ aliphatic mono- or polyalcohols, the total carbon number of the esters being greater than or equal to 10.

Among the monoesters, non-limiting mention may be made of dihydroabietyl behenate; octyldodecyl behenate; isocetyl behenate; cetyl lactate; $C_{12}$-$C_{15}$ alkyl lactate; isostearyl lactate; lauryl lactate; linoleyl lactate; oleyl lactate; (iso)stearyl octanoate; isocetyl octanoate; octyl octanoate; cetyl octanoate; decyl oleate; isocetyl isostearate; isocetyl laurate; isocetyl stearate; isodecyl octanoate; isodecyl oleate; isononyl isononanoate; isostearyl palmitate; methylacetyl ricinoleate; myristyl stearate; octyl isononanoate; 2-ethylhexyl isononate; octyl palmitate; octyl pelargonate; octyl stearate; octyldodecyl erucate; oleyl erucate; ethyl and isopropyl palmitates, 2-ethylhexyl palmitate, 2-octyldecyl palmitate, alkyl myristates such as isopropyl, butyl, cetyl, 2-octyldodecyl, myristyl or stearyl myristate, hexyl stearate, butyl stearate, isobutyl stearate; dioctyl malate, hexyl laurate, and 2-hexyldecyl laurate.

In some embodiments, esters of $C_4$-$C_{22}$ dicarboxylic or tricarboxylic acids and of $C_1$-$C_{22}$ alcohols and esters of mono-, di- or tricarboxylic acids and of $C_2$-$C_{26}$ di-, tri-, tetra- or pentahydroxy alcohols may also be used.

The following non-limiting examples may also be mentioned: diethyl sebacate; diisopropyl sebacate; diisopropyl adipate; di-n-propyl adipate; dioctyl adipate; diisostearyl adipate; dioctyl maleate; glyceryl undecylenate; octyldodecyl stearoyl stearate; pentaerythrityl monoricinoleate; pentaerythrityl tetraisononanoate; pentaerythrityl tetrapelargonate; pentaerythrityl tetraisostearate; pentaerythrityl tetraoctanoate; propylene glycol dicaprylate; propylene glycol dicaprate; tridecyl erucate; triisopropyl citrate; triisostearyl citrate; glyceryl trilactate; glyceryl trioctanoate; trioctyldodecyl citrate; trioleyl citrate; propylene glycol dioctanoate; neopentyl glycol diheptanoate; diethylene glycol diisononanoate; and polyethylene glycol distearates.

Among the esters mentioned above, in some embodiments, ethyl, isopropyl, myristyl, cetyl or stearyl palmitate, 2-ethylhexyl palmitate, 2-octyldecyl palmitate, alkyl myristates such as isopropyl, butyl, cetyl or 2-octyldodecyl myristate, hexyl stearate, butyl stearate, isobutyl stearate; dioctyl malate, hexyl laurate, 2-hexyldecyl laurate, isononyl isononanoate and cetyl octanoate may for example be used.

The composition described herein may also comprise, as fatty ester, sugar esters and diesters of $C_6$-$C_{30}$ and for example $C_{12}$-$C_{22}$ fatty acids. As used herein, the term "sugar" means oxygen-bearing hydrocarbon-based compounds having several alcohol functions, with or without aldehyde or ketone functions, and which contain at least 4 carbon atoms. These sugars may be monosaccharides, oligosaccharides, or polysaccharides.

Non-limiting examples of sugars that may be mentioned include sucrose (or saccharose), glucose, galactose, ribose, fructose, maltose, mannose, arabinose, xylose and lactose, and the derivatives thereof, for example alkyl derivatives, such as methyl derivatives, for instance methylglucose.

In some embodiments, the sugar esters of fatty acids may be chosen for example from the group comprising the esters or mixtures of esters of sugars described herein and of linear or branched, saturated or unsaturated $C_6$-$C_{30}$ and for example $C_{12}$-$C_{22}$ fatty acids. If they are unsaturated, these compounds may comprise one to three conjugated or nonconjugated carbon-carbon double bonds.

In some embodiments, the esters may also be chosen from mono-, di-, tri-, tetraesters and polyesters, and mixtures thereof.

In some embodiments, the esters may be chosen, for example, from oleates, laurates, palmitates, myristates, behenates, cocoates, stearates, linoleates, linolenates, caprates and arachidonates, and mixtures thereof such as, for example, oleo-palmitate, oleo-stearate and palmito-stearate mixed esters.

In some embodiments, monoesters and diesters and for example sucrose, glucose or methylglucose mono- or dioleates, stearates, behenates, oleopalmitates, linoleates, linolenates and oleostearates may for example be used.

A non-limiting example that may be mentioned is the product sold under the name Glucate® DO by the company Amerchol, which is a methylglucose dioleate.

Non-limiting examples of esters or mixtures of esters of sugar and of fatty acid that may also be mentioned include:

the products sold under the names F160, F140, F110, F90, F70 and SL40 by the company Crodesta, respectively denoting sucrose palmitostearates formed from 73% monoester and 27% diester and triester, from 61% monoester and 39% diester, triester and tetraester, from 52% monoester and 48% diester, triester and tetraester, from 45% monoester and 55% diester, triester and tetraester, from 39% monoester and 61% diester, triester and tetraester, and sucrose monolaurate;

the products sold under the name Ryoto Sugar Esters, for example referenced B370 and corresponding to sucrose behenate formed from 20% monoester and 80% di-triesterpolyester; and the sucrose mono-dipalmito-stearate sold by the company Goldschmidt under the name Tegosoft® PSE.

In some embodiments, the non-silicone wax(es) may be chosen for example from carnauba wax, candelilla wax, esparto grass wax, paraffin wax, ozokerite, plant waxes such as olive wax, rice wax, hydrogenated jojoba wax or the absolute waxes of flowers such as the essential wax of blackcurrant blossom sold by the company Bertin (France), animal waxes, for instance beeswaxes or modified beeswaxes (cerabellina); other waxes or waxy starting materials that may be used in the process described herein are for example marine waxes such as the product sold by the company Sophim under the reference M82, and polyethylene waxes or waxes of polyolefins in general.

In some embodiments, the silicones that may be used in the cosmetic compositions described herein may be volatile or non-volatile, cyclic, linear or branched silicones, which are unmodified or modified with organic groups, having a viscosity from $5\times10^{-6}$ to $2.5\,m^2/s$ at $25°\,C$., such as $1\times10^{-5}$ to $1\,m^2/s$.

In some embodiments, the silicones that may be used in the process described herein may be in the form of oils, waxes, resins or gums.

In some embodiments, the silicone may be chosen from polydialkylsiloxanes, such as polydimethylsiloxanes (PDMS), and organomodified polysiloxanes comprising at least one functional group chosen from poly(oxyalkylene) groups, amino groups and alkoxy groups.

In some embodiments, the organopolysiloxanes may be defined in greater detail in Walter Noll's "Chemistry and Technology of Silicones" (1968) Academic Press. They may be volatile or non-volatile.

When they are volatile, in some embodiments, the silicones may for example be chosen from those having a boiling point ranging from $60°\,C$. to $260°\,C$., for example from (i) cyclic polydialkylsiloxanes having from 3 to 7 and for example 4 to 5 silicon atoms. These are, for example, octamethylcyclotetrasiloxane sold under the name Volatile Silicone® 7207 by Union Carbide or Silbione® 70045 V2 by Rhodia, decamethylcyclopentasiloxane sold under the name Volatile Silicone® 7158 by Union Carbide, and Silbione® 70045 V5 by Rhodia, and mixtures thereof.

Non-limiting mention may also be made of cyclocopolymers of the dimethylsiloxane/methylalkylsiloxane type, such as Volatile Silicone® FZ 3109 sold by the company Union Carbide, of formula:

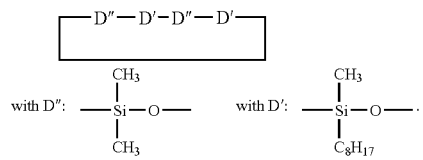

Non-limiting mention may also be made of mixtures of cyclic polydialkylsiloxanes with organosilicon compounds, such as the mixture of octamethylcyclotetrasiloxane and tetratrimethylsilylpentaerythritol (50/50) and the mixture of octamethylcyclotetrasiloxane and oxy-1,1'-bis(2,2,2',2',3,3'-hexatrimethylsilyloxy)-neopentane.

Additional non-limiting examples of volatile silicones include (ii) linear volatile polydialkylsiloxanes having 2 to 9 silicon atoms and having a viscosity of less than or equal to $5 \times 10^{-6}$ m$^2$/s at 25° C. An example is decamethyltetrasiloxane sold under the name SH 200 by the company Toray Silicone. Silicones belonging to this category are also described in the article published in Cosmetics and Toiletries, Vol. 91, Jan. 76, pp. 27-32, Todd & Byers "Volatile Silicone Fluids for Cosmetics".

In some embodiments, non-volatile polydialkylsiloxanes, polydialkylsiloxane gums and resins, polyorganosiloxanes modified with the above organofunctional groups, and mixtures thereof, may for example be used.

In some embodiments, these silicones may for example be chosen from polydialkylsiloxanes, among which non-limiting mention may be made of polydimethylsiloxanes having trimethylsilyl end groups. The viscosity of the silicones may be measured, for example, at 25° C. according to ASTM standard 445 Appendix C.

Among these polydialkylsiloxanes, mention may be made, in a non-limiting manner, of the following commercial products:

the Silbione® oils of the 47 and 70 047 series or the Mirasil® oils sold by Rhodia, for instance the oil 70 047 V 500 000;

the oils of the Mirasil® series sold by the company Rhodia;

the oils of the 200 series from the company Dow Corning, such as DC200 with a viscosity of 60 000 mm$^2$/s;

the Viscasil® oils from General Electric and certain oils of the SF series (SF 96, SF 18) from General Electric.

Non-limiting mention may also be made of polydimethylsiloxanes having dimethylsilanol end groups known under the name Dimethiconol (CTFA), such as the oils of the 48 series from the company Rhodia.

In this category of polydialkylsiloxanes, non-limiting mention may also be made of the products sold under the names Abil Wax® 9800 and 9801 by the company Goldschmidt, which are poly($C_1$-$C_{20}$)dialkylsiloxanes.

In some embodiments, the silicone gums that can be used in the process described herein may for example be polydialkylsiloxanes and polydimethylsiloxanes with high number-average molecular masses ranging from 200,000 to 1,000,000, used alone or as a mixture in a solvent. This solvent can be chosen from volatile silicones, polydimethylsiloxane (PDMS) oils, polyphenylmethylsiloxane (PPMS) oils, isoparaffins, polyisobutylenes, methylene chloride, pentane, dodecane and tridecane, and mixtures thereof.

In some embodiments, products that can be used for example in the process described herein are mixtures such as:

mixtures formed from a polydimethylsiloxane hydroxylated at the chain end, or dimethiconol (CTFA) and from a cyclic polydimethylsiloxane also known as cyclomethicone (CTFA), such as the product Q2 1401 sold by the company Dow Corning;

mixtures formed from a polydimethylsiloxane gum with a cyclic silicone, such as the product SF 1214 Silicone Fluid from the company General Electric; this product is an SF 30 gum corresponding to a dimethicone, having a number-average molecular weight of 500 000, dissolved in the oil SF 1202 Silicone Fluid corresponding to decamethylcyclopentasiloxane;

mixtures of two PDMSs with different viscosities, for example of a PDMS gum and a PDMS oil, such as the product SF 1236 from the company General Electric. The product SF 1236 is a mixture of an SE 30 gum defined above, having a viscosity of 20 m$^2$/s, and an SF 96 oil, with a viscosity of $5 \times 10^{-6}$ m$^2$/s. In some embodiments, this product may contain for example 15% SE 30 gum and 85% SF 96 oil.

In some embodiments, the organopolysiloxane resins that can be used in the process described herein may be for example crosslinked siloxane systems having the following units:

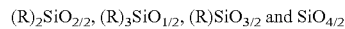

wherein each R independently represents an alkyl having 1 to 16 carbon atoms. Among these products, those in which each R independently denotes a $C_1$-$C_4$ lower alkyl radical, such as methyl, may for example be used.

In some embodiments, among these resins, non-limiting mention may be made of the product sold under the name Dow Corning 593 or those sold under the names Silicone Fluid SS 4230 and SS 4267 by the company General Electric, which are silicones of dimethyl/trimethyl siloxane structure.

Non-limiting mention may also be made of trimethyl siloxysilicate type resins sold for instance under the names X22-4914, X21-5034 and X21-5037 by the company Shin-Etsu.

The organomodified silicones that can be used in the process described herein are silicones as defined above and comprising in their structure at least one organofunctional group attached via a hydrocarbon-based group.

Besides the silicones described above, the organomodified silicones may be for example be polydiarylsiloxanes, such as polydiphenylsiloxanes, and polyalkylaryl-siloxanes functionalized with the organofunctional groups mentioned previously.

The polyalkylarylsiloxanes may be chosen for example from linear and/or branched polydimethyl/methylphenylsiloxanes and polydimethyl/diphenylsiloxanes with a viscosity ranging from $1 \times 10^{-5}$ to $5 \times 10^{-2}$ m$^2$/s at 25° C.

Among these polyalkylarylsiloxanes, non-limiting examples that may be mentioned include the products sold under the following names:

the Silbione® oils of the 70 641 series from Rhodia;

the oils of the Rhodorsil® 70 633 and 763 series from Rhodia;

the oil Dow Corning 556 Cosmetic Grade Fluid from Dow Corning;

the silicones of the PK series from Bayer, such as the product PK20;

the silicones of the PN and PH series from Bayer, such as the products PN1000 and PH1000;

certain oils of the SF series from General Electric, such as SF 1023, SF 1154, SF 1250 and SF 1265.

Among the organomodified silicones, non-limiting mention may be made of polyorganosiloxanes comprising:

polyethyleneoxy and/or polypropyleneoxy groups optionally comprising $C_6$-$C_{24}$ alkyl groups, such as the products known as dimethicone copolyol sold by the company Dow Corning under the name DC 1248 or the oils Silwet® L 722, L 7500, L 77 and L 711 by the company Union Carbide, and the ($C_{12}$)alkylmethicone copolyol sold by the company Dow Corning under the name Q2 5200;

substituted or unsubstituted amine groups, such as the products sold under the name GP 4 Silicone Fluid and GP 7100 by the company Genesee, or the products sold under the names Q2 8220 and Dow Corning 929 or 939 by the company Dow Corning. The substituted amine groups may, for example, be $C_1$-$C_4$ aminoalkyl groups; and alkoxylated groups such as the product sold under the name Silicone Copolymer F-755 by SWS Silicones, and Abil Wax® 2428, 2434 and 2440 by the company Goldschmidt.

In some embodiments, the at least one fatty substance does not comprise any $C_2$-$C_3$ oxyalkylene units or any glycerolic units.

In some embodiments, the at least one fatty substance may be chosen from compounds that are liquid or pasty at room temperature and at atmospheric pressure.

In some embodiments, the at least one fatty substance may be a compound that is liquid at a temperature of 25° C. and at atmospheric pressure.

In some embodiments, the at lest one fatty substance is different from fatty acids.

The at least one fatty substance may for example be chosen from $C_8$-$C_{16}$ lower alkanes, non-silicone oils of plant, mineral or synthetic origin, fatty alcohols, esters of a fatty acid and/or of a fatty alcohol, and silicones.

In some embodiments, the at least one fatty substance of the composition according to the process described herein may be non-silicone.

In some embodiments, the at least one fatty substance may be chosen from liquid petroleum jelly, polydecenes and liquid esters of a fatty acid and/or of a fatty alcohol, and mixtures thereof.

In some embodiments, the at least one anhydrous composition (A) comprises at least one fatty substance present in an amount ranging from 10% to 99% by weight, for example from 20% to 90% by weight, such as from 25% to 80% by weight, relative to the weight of the at least one anhydrous composition (A).

The at least one anhydrous cosmetic composition (A) also comprises at least one surfactant.

In some embodiments, the at least one surfactant may be chosen from at least one nonionic surfactant and at least one anionic surfactant.

The at least one anionic surfactant may for example be chosen from the salts (for example alkali metal salts, such as sodium salts, ammonium salts, amine salts, amino alcohol salts or alkaline-earth metal salts such as magnesium salts) of the following compounds:

alkyl sulfates, alkyl ether sulfates, alkylamido ether sulfates, alkylaryl polyether sulfates, and monoglyceride sulfates;

alkylsulfonates, alkylamidesulfonates, alkylarylsulfonates, α-olefin sulfonates, and paraffin sulfonates;

alkyl phosphates, and alkyl ether phosphates;

alkylsulfosuccinates, alkyl ether sulfosuccinates, and alkylamidesulfosuccinates;

alkylsulfoacetates;

acylsarcosinates; acylisethionates, and N-acyltaurates;

salts of fatty acids such as oleic acid, ricinoleic acid, palmitic acid or stearic acid, coconut oil acid or hydrogenated coconut oil acid;

alkyl-D-galactoside uronic acid salts;

acyllactylates;

salts of polyoxyalkylenated alkyl ether carboxylic acids, of polyoxyalkylenated alkylaryl ether carboxylic acids or of polyoxyalkylenated alkylamido ether carboxylic acids, for instance those having from 2 to 50 ethylene oxide groups;

and mixtures thereof.

It should be noted that the alkyl or acyl radical of these various compounds may for example have from 6 to 24 carbon atoms, such as from 8 to 24 carbon atoms, and the aryl radical may for example denote a phenyl or benzyl group.

The at least one nonionic surfactant may for example be chosen from monooxyalkylenated, polyoxyalkylenated, monoglycerolated, and polyglycerolated nonionic surfactants. The oxyalkylene units may for example be oxyethylene or oxypropylene units, or a combination thereof, for example oxyethylene units.

Non-limiting examples of oxyalkylenated nonionic surfactants that may be mentioned include:

oxyalkylenated ($C_8$-$C_{24}$)alkylphenols, saturated or unsaturated, linear or branched, oxyalkylenated $C_8$-$C_{30}$ alcohols, saturated or unsaturated, linear or branched, oxyalkylenated $C_8$-$C_{30}$ amides, esters of saturated or unsaturated, linear or branched, $C_8$-$C_{30}$ acids and of polyethylene glycols, polyoxyethylenated esters of saturated or unsaturated, linear or branched, $C_8$-$C_{30}$ acids and of sorbitol, saturated or unsaturated, oxyethylenated plant oils, and condensates of ethylene oxide and/or of propylene oxide, inter alia, alone or as mixtures.

In some embodiments, the surfactants may contain a number of moles of ethylene oxide and/or of propylene oxide ranging from 1 to 100 such as from 2 to 50. In some embodiments, the at least one nonionic surfactant does not comprise any oxypropylene units.

In some embodiments, the oxyalkylenated nonionic surfactants may for example be chosen from oxyethylenated $C_8$-$C_{30}$ alcohols, and polyoxyethylenated esters of saturated or unsaturated, linear or branched $C_8$-$C_{30}$ acids, and of sorbitol.

As non-limiting examples of monoglycerolated or polyglycerolated nonionic surfactants, monoglycerolated or polyglycerolated $C_8$-$C_{40}$ alcohols may for example be used.

In some embodiments, the monoglycerolated or polyglycerolated $C_8$-$C_{40}$ alcohols may correspond to the following formula:

$$RO-[CH_2-CH(CH_2OH)-O]_m-H$$

wherein R represents a linear or branched $C_8$-$C_{40}$ such as $C_8$-$C_{30}$ alkyl or alkenyl radical, and m represents a number ranging from 1 to 30, such as from 1 to 10.

As non-limiting examples of compounds that may be used in the process described herein, mention may be made of lauryl alcohol containing 4 mol of glycerol (INCI name: Polyglyceryl-4 Lauryl Ether), lauryl alcohol containing 1.5 mol of glycerol, oleyl alcohol containing 4 mol of glycerol (INCI name: Polyglyceryl-4 Oleyl Ether), oleyl alcohol containing 2 mol of glycerol (INCI name: Polyglyceryl-2 Oleyl Ether), cetearyl alcohol containing 2 mol of glycerol, cetearyl alcohol containing 6 mol of glycerol, oleocetyl alcohol containing 6 mol of glycerol, and octadecanol containing 6 mol of glycerol.

The alcohol may represent a mixture of alcohols in the same way that the value of m represents a statistical value, which means that, in a commercial product, several species of polyglycerolated fatty alcohol may coexist in the form of a mixture.

In some embodiments, among the monoglycerolated or polyglycerolated alcohols, $C_8/C_{10}$ alcohol containing 1 mol of glycerol, $C_{10}/C_{12}$ alcohol containing 1 mol of glycerol and $C_{12}$ alcohol containing 1.5 mol of glycerol may for example be used.

In some embodiments, the at least one surfactant present in the at least one anhydrous composition (A) is a nonionic surfactant.

The at least one surfactant may be present in the at least one anhydrous composition (A) in an amount ranging from 0.1% to 50% by weight, such as from 0.5% to 30% by weight, relative to the weight of the at least one anhydrous composition (A).

The at least one anhydrous composition (A) may further comprise various adjuvants conventionally used in hair dyeing compositions, such as anionic, cationic, nonionic, amphoteric or zwitterionic polymers and mixtures thereof; mineral thickeners, for example fillers such as clays, talc; organic thickeners with, for instance, anionic, cationic, nonionic and amphoteric polymeric associative thickeners; antioxidants; penetrants; sequestrants; fragrances; dispersants; film-forming agents; conditioning agents; ceramides; preserving agents; and opacifiers.

In some embodiments, the above adjuvants may each for example be present in an amount ranging from 0.01% to 20% by weight relative to the weight of the at least one anhydrous composition (A).

In some embodiments, the composition described herein may comprise at least one mineral thickener chosen from organophilic clays, fumed silicas, and mixtures thereof.

The organophilic clay may be chosen from montmorillonite, bentonite, hectorite, attapulgite, sepiolite, and mixtures thereof. For example, the clay may be a bentonite or a hectorite.

In some embodiments, these clays may be modified with a chemical compound chosen from quaternary amines, tertiary amines, amine acetates, imidazolines, amine soaps, fatty sulfates, alkyl aryl sulfonates and amine oxides, and mixtures thereof.

Organophilic clays that may be mentioned in a non-limiting manner include quaternium-18 bentonites such as those sold under the names Bentone 3, Bentone 38 and Bentone 38V by the company Rheox, Tixogel VP by the company United Catalyst, Claytone 34, Claytone 40 and Claytone XL by the company Southern Clay; stearalkonium bentonites such as those sold under the names Bentone 27 by the company Rheox, Tixogel LG by the company United Catalyst, and Claytone AF and Claytone APA by the company Southern Clay; quaternium-18/benzalkonium bentonites such as those sold under the names Claytone HT and Claytone PS by the company Southern Clay; quaternium-18 hectorites such as those sold under the names Bentone Gel DOA, Bentone Gel ECO5, Bentone Gel EUG, Bentone Gel IPP, Bentone Gel ISD, Bentone Gel SS71, Bentone Gel VS8 and Bentone Gel VS38 by the company Rheox, and Simagel M and Simagel S1345 by the company Biophil.

In some embodiments, the fumed silicas may be obtained by high-temperature hydrolysis of a volatile silicon compound in an oxhydric flame, producing a finely divided silica. This process may make it possible for example to obtain hydrophilic silicas having a large number of silanol groups at their surface. Such hydrophilic silicas are sold, for example, under the names Aerosil 130®, Aerosil 200®, Aerosil 255®, Aerosil 300® and Aerosil 380® by the company Degussa, and Cab-O-Sil HS-5®, Cab-O-Sil EH-5®, Cab-O-Sil LM-130®, Cab-O-Sil MS-55 and Cab-O-Sil M-5® by the company Cabot.

In some embodiments, it may be possible to chemically modify the surface of the silica, via a chemical reaction generating a reduction in the number of silanol groups. In some embodiments, it may for example be possible to substitute silanol groups with hydrophobic groups: a hydrophobic silica is then obtained.

The hydrophobic groups may be chosen from:

trimethylsiloxyl groups, which may be obtained for example by treating fumed silica in the presence of hexamethyldisilazane. Silicas thus treated are known as "silica silylate" according to the CTFA (6th Edition, 1995). They are sold, for example, under the references Aerosil R812® by the company Degussa and Cab-O-Sil TS-530® by the company Cabot; and dimethylsilyloxyl or polydimethylsiloxane groups, which may be obtained for example by treating fumed silica in the presence of polydimethylsiloxane or dimethyldichlorosilane. Silicas thus treated are known as "silica dimethyl silylate" according to the CTFA (6th Edition, 1995). They are sold, for example, under the references Aerosil R972® and Aerosil R974® by the company Degussa, and Cab-O-Sil TS-610® and Cab-O-Sil TS-720® by the company Cabot.

In some embodiments, the fumed silica may have a particle size that may be nanometric to micrometric, for example ranging from about 5 to 200 nm.

In some embodiments, the composition described herein comprises a hectorite, an organomodified bentonite, or an optionally modified fumed silica.

When it is present, the mineral thickener may be present in an amount ranging from 1% to 30% by weight, relative to the weight of the composition.

As indicated previously, the at least one composition (B) used in the process described herein comprises monoethanolamine and at least one basic amino acid.

The at least one basic amino acid that may be used in the process described herein may for example be chosen from those comprising an additional amine function optionally included in a ring or a ureido function.

In some embodiments, the at least one basic amino acid may for example be chosen from those corresponding to formula (I) below:

(I)

wherein R denotes a group chosen from:

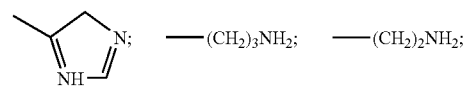

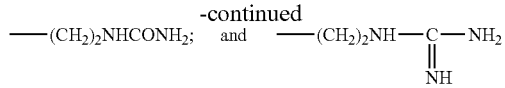

The basic amino acids corresponding to formula (I) may for example be histidine, lysine, arginine, ornithine and citrulline, and for instance arginine, lysine and histidine, or mixtures thereof.

In some embodiments, the at least one composition (B) comprises monoethanolamine present in an amount ranging from 0.1% to 40% by weight, such as from 0.5% to 20% by weight, relative to the weight of the at least one composition (B).

In some embodiments, the at least one basic amino acid is present in an amount ranging from 0.1% to 40% by weight, such as from 0.5% to 20% by weight, relative to the weight of the at least one composition (B).

In some embodiments, the weight ratio of the monoethanolamine and the at least one basic amino acid present is the at least one composition (B) has a value ranging from 0.1 to 10, for example from 0.3 to 10, such as from 1 to 5.

In some embodiments, when the process described herein is a process for dyeing keratin fibers, the at least one composition (B) also comprises at least one oxidation dye and/or at least one direct dye.

The at least one oxidation dye may for example be chosen from at least one oxidation base optionally combined with at least one coupler.

By way of non-limiting example, the at least one oxidation base may be chosen from para-phenylenediamines, bis(phenyl)alkylenediamines, para-aminophenols, ortho-aminophenols and heterocyclic bases, and the addition salts thereof.

Among the para-phenylenediamines that may be mentioned in a non-limiting manner, for example, are para-phenylenediamine, para-toluenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(3-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N,N-(β-hydroxyethyl)-para-phenylenediamine, N-(3,7-dihydroxypropyl)-para-phenylenediamine, N-(4'-aminophenyl)-para-phenylenediamine, N-phenyl-para-phenylenediamine, 2-β-hydroxy-ethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene and 3-hydroxy-1-(4'-aminophenyl)pyrrolidine, and the addition salts thereof with an acid.

Among the para-phenylenediamines mentioned above, para-phenylenediamine, para-toluenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine, and the addition salts thereof with an acid, may for example be used.

Among the bis(phenyl)alkylenediamines that may be mentioned in a non-limiting manner, for example, are N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetra-methylenediamine, N,N'-bis(ethyl)-N,N'-bis(4'-amino-3'-methylphenyl)ethylenediamine and 1,8-bis(2,5-diaminophenoxy)-3,6-dioxaoctane, and the addition salts thereof.

Among the para-aminophenols that may be mentioned in a non-limiting manner, for example, are para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and the addition salts thereof with an acid.

Among the ortho-aminophenols that may be mentioned in a non-limiting manner, for example, are 2-aminophenol, 2-amino-5-methylphenol, 2-amino-6-methylphenol and 5-acetamido-2-aminophenol, and the addition salts thereof.

Among the heterocyclic bases that may be mentioned in a non-limiting manner, for example, are pyridine derivatives, pyrimidine derivatives and pyrazole derivatives.

Among the pyridine derivatives that may be mentioned in a non-limiting manner are the pyridine derivatives described, for example, in patents GB 1 026 978 and GB 1 153 196, for instance 2,5-diaminopyridine, 2-(4-methoxyphenyl)amino-3-amino-pyridine and 3,4-diaminopyridine, and the addition salts thereof.

Other pyridine oxidation bases that are useful in the process described herein are the 3-aminopyrazolo[1,5-a]pyridine oxidation bases and the addition salts thereof described, for example, in patent application FR 2 801 308. Non-limiting examples that may be mentioned include pyrazolo[1,5-a]pyrid-3-ylamine, 2-acetylaminopyrazolo[1,5-a]pyrid-3-ylamine, 2-morpholin-4-ylpyrazolo[1,5-a]pyrid-3-ylamine, 3-aminopyrazolo[1,5-a]pyridine-2-carboxylic acid, 2-methoxypyrazolo[1,5-a]pyrid-3-ylamine, (3-aminopyrazolo[1,5-a]pyrid-7-yl)methanol, 2-(3-aminopyrazolo[1,5-a]pyrid-5-yl)ethanol, 2-(3-aminopyrazolo[1,5-a]pyrid-7-yl)ethanol, (3-aminopyrazolo[1,5-a]pyrid-2-yl)methanol, 3,6-diaminopyrazolo[1,5-a]pyridine, 3,4-diaminopyrazolo[1,5-a]pyridine, pyrazolo[1,5-a]pyridine-3,7-diamine, 7-morpholin-4-ylpyrazolo[1,5-a]pyrid-3-ylamine, pyrazolo[1,5-a]pyridine-3,5-diamine, 5-morpholin-4-ylpyrazolo[1,5-a]pyrid-3-ylamine, 2-[(3-aminopyrazolo[1,5-a]pyrid-5-yl)(2-hydroxyethyl)amino]ethanol, 2-[(3-aminopyrazolo[1,5-a]pyrid-7-yl)(2-hydroxyethyl)amino]ethanol, 3-aminopyrazolo[1,5-a]pyridin-5-ol, 3-aminopyrazolo[1,5-a]pyridin-4-ol, 3-aminopyrazolo[1,5-a]pyridin-6-ol and 3-aminopyrazolo[1,5-a]pyridin-7-ol, and the addition salts thereof.

Among the pyrimidine derivatives that may be mentioned in a non-limiting manner are the pyrimidine derivatives described, for example, in patents DE 2 359 399; JP 88-169 571; JP 05-63124; EP 0 770 375 or patent application WO 96/15765, for instance 2,4,5,6-tetraminopyrimidine, 4-hydroxy-2,5,6-triaminopyrimidine, 2-hydroxy-4,5,6-triaminopyrimidine, 2,4-dihydroxy-5,6-diaminopyrimidine and 2,5,6-triaminopyrimidine, and the addition salts thereof, and the tautomeric forms thereof, when a tautomeric equilibrium exists.

Among the pyrazole derivatives that may be mentioned in a non-limiting manner are the pyrazole derivatives described in patents DE 3 843 892 and DE 4 133 957, and patent applications WO 94/08969, WO 94/08970, FR-A-2 733 749 and DE 195 43 988, for instance 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methyl-pyrazole, 4,5-diamino-3-tert-butyl-1-methylpyrazole, 4,5-diamino-1-tert-butyl-3-methyl-pyrazole, 4,5-diamino-1-(β-hydroxyethyl)-3-methylpyrazole, 4,5-diamino-1-ethyl-3-methyl-pyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole and 3,5-diamino-4-(β-hydroxyethyl)amino-1-methylpyrazole, and the addition salts thereof. 4,5-diamino-1-(β-methoxyethyl)pyrazole for example may also be used.

In some embodiments, a 4,5-diaminopyrazole may for example be used, and for example 4,5-diamino-1-(β-hydroxyethyl)pyrazole and/or a salt thereof.

Pyrazole derivatives that may also be mentioned in a non-limiting manner include diamino-N,N-dihydropyrazolopyrazolones and for example those described in patent application FR-A-2 886 136, such as the following compounds and the addition salts thereof: 2,3-diamino-6,7-dihydro-1H,5H-pyrazolo[1,2-a]pyrazol-1-one, 2-amino-3-ethyl-amino-6,7-dihydro-1H,5H-pyrazolo[1,2-a]pyrazol-1-one, 2-amino-3-isopropylamino-6,7-dihydro-1H,5H-pyrazolo[1,2-a]pyrazol-1-one, 2-amino-3-(pyrrolidin-1-yl)-6,7-dihydro-1H,5H-pyrazolo[1,2-a]pyrazol-1-one, 4,5-diamino-1,2-dimethyl-1,2-dihydropyrazol-3-one, 4,5-diamino-1,2-diethyl-1,2-dihydropyrazol-3-one, 4,5-diamino-1,2-di-(2-hydroxyethyl)-1,2-dihydropyrazol-3-one, 2-amino-3-(2-hydroxyethyl)amino-6,7-dihydro-1H,5H-pyrazolo[1,2-a]pyrazol-1-one, 2-amino-3-dimethylamino-6,7-dihydro-1H,5H-pyrazolo[1,2-a]pyrazol-1-one, 2,3-diamino-5,6,7,8-tetrahydro-1H,6H-pyridazino[1,2-a]pyrazol-1-one, 4-amino-1,2-diethyl-5-(pyrrolidin-1-yl)-1,2-dihydropyrazol-3-one, 4-amino-5-(3-dimethylaminopyrrolidin-1-yl)-1,2-diethyl-1,2-dihydropyrazol-3-one, 2,3-diamino-6-hydroxy-6,7-dihydro-1H,5H-pyrazolo[1,2-a]pyrazol-1-one.

In some embodiments, 2,3-Diamino-6,7-dihydro-1H,5H-pyrazolo[1,2-a]pyrazol-1-one and/or a salt thereof may for example be used.

In some embodiments, a heterocyclic base that may also be used includes 4,5-diamino-1-(β-hydroxyethyl)pyrazole and/or 2,3-diamino-6,7-dihydro-1H,5H-pyrazolo[1,2-a]pyrazol-1-one and/or a salt thereof.

In some embodiments, the at least one composition (B) of the dyeing process described herein may optionally comprise at least one coupler chosen from those conventionally used for the dyeing of keratin fibers.

Among these couplers, non-limiting mention may be made for example of meta-phenylenediamines, meta-aminophenols, meta-diphenols, naphthalene-based couplers and heterocyclic couplers, and the addition salts thereof.

Non-limiting mention may be made, for example, of 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(3-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methyl-indole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene, 2,6-bis(β-hydroxyethylamino)toluene, 6-hydroxyindoline, 2,6-dihydroxy-4-methylpyridine, 1-H-3-methylpyrazol-5-one, 1-phenyl-3-methylpyrazol-5-one, 2,6-dimethylpyrazolo[1,5-b]-1,2,4-triazole, 2,6-dimethyl[3,2-c]-1,2,4-triazole and 6-methylpyrazolo[1,5-a]benzimidazole, the addition salts thereof with an acid, and mixtures thereof.

In general, the addition salts of the at least one oxidation base and the at least one coupler that may be used in the process described herein may for example be chosen from the addition salts with an acid such as the hydrochlorides, hydrobromides, sulfates, citrates, succinates, tartrates, lactates, tosylates, benzenesulfonates, phosphates, and acetates.

The at least one oxidation base may each be present in an amount ranging from 0.0001% to 10% by weight relative to the total weight of the at least one composition (B), such as from 0.005% to 5% by weight relative to the total weight of the at least one composition (B).

The at least one coupler, if they are present, may each be present in an amount ranging from 0.0001% to 10% by weight, relative to the total weight of the at least one composition (B), such as from 0.005% to 5% by weight, relative to the total weight of the at least one composition (B).

In some embodiments, the at least one composition (B) of the dyeing process described herein may also comprise at least one direct dye.

As regards the direct dyes, the at least one dye may for example be chosen from ionic and nonionic species, such as cationic or nonionic species.

Non-limiting examples of the at least one direct dye that may be mentioned include the following direct dyes: azo dyes; methine dyes; carbonyl dyes; azine dyes; nitro (hetero) aryl dyes; tri(hetero)arylmethane dyes; porphyrin dyes; phthalocyanin dyes, and natural direct dyes, alone or as mixtures.

In some embodiments, the azo dyes may comprise an —N=N— function, the two nitrogen atoms of which are not simultaneously engaged in a ring. However, one of the two nitrogen atoms of the sequence —N=N— may be engaged in a ring.

The dyes of the methine family may for example be compounds comprising at least one sequence chosen from >C=C< and —N=C<, the two atoms of which are not simultaneously engaged in a ring. However, one of the nitrogen or carbon atoms of the sequences may be engaged in a ring. For example, the dyes of this family may be derived from compounds of the type such as methines, azomethines, mono- and diarylmethanes, indoamines (or diphenylamines), indophenols, indoanilines, carbocyanins, azacarbocyanins and isomers thereof, diazacarbocyanins and isomers thereof, tetraazacarbocyanins and hemicyanins.

As regards the dyes of the carbonyl family, non-limiting examples that may be mentioned include dyes chosen from acridone, benzoquinone, anthraquinone, naphthoquinone, benzanthrone, anthranthrone, pyranthrone, pyrazolanthrone, pyrimidinoanthrone, flavanthrone, idanthrone, flavone, (iso) violanthrone, isoindolinone, benzimidazolone, isoquinolinone, anthrapyridone, pyrazoloquinazolone, perinone, quinacridone, quinophthalone, indigoid, thioindigo, naphthalimide, anthrapyrimidine, diketopyrrolopyrrole and coumarin.

As regards the dyes of the cyclic azine family, non-limiting mention may be made for example of azine, xanthene, thioxanthene, fluorindine, acridine, (di)oxazine, (di)thiazine and pyronin.

The nitro (hetero)aromatic dyes may for example be nitrobenzene or nitropyridine direct dyes.

As regards the dyes of porphyrin or phthalocyanin type, it may be possible to use cationic or non-cationic compounds, optionally comprising at least one metal or metal ion, for instance alkali metals, alkaline-earth metals, zinc and silicon.

Non-limiting examples of the at least one direct dye that may be mentioned include nitrobenzene dyes; azo direct dyes; azomethine direct dyes; methine direct dyes; azacarbocyanin direct dyes, for instance tetraazacarbocyanins (tetraazapentamethines); quinone and for example anthraquinone, naphthoquinone or benzoquinone direct dyes; azine; xanthene; triarylmethane; indoamine; indigoid; phthalocyanin and porphyrin direct dyes, and natural direct dyes, alone or as mixtures.

In some embodiments, these dyes may be monochromophoric dyes (i.e. comprising only one dye) or polychromophoric, such as di- or trichromophoric; the chromophores possibly being identical or different, and from the same chemical family or otherwise. It should be noted that a polychromophoroc dye may comprise several radicals each derived from a molecule that absorbs in the visible region ranging from 400 to 800 nm. Furthermore, this absorbance of the dye may not require any prior oxidation thereof, or combination with any other chemical species.

In the case of polychromophoric dyes, in some embodiments, the chromophores may be connected together by means of at least one linker, which may be cationic or non-cationic.

In some embodiments, the linker may be a linear, branched or cyclic $C_1$-$C_{20}$ alkyl chain, optionally interrupted with at least one heteroatom (such as nitrogen or oxygen) and/or with at least one group comprising such an atom (CO, $SO_2$), optionally interrupted with at least one heterocycle that may or may not be fused to a phenyl nucleus and comprising at least one quaternized nitrogen atom engaged in the said ring and optionally at least one other heteroatom (such as oxygen, nitrogen or sulfur), optionally interrupted with at least one substituted or unsubstituted phenyl or naphthyl group, optionally at least one quaternary ammonium group substituted with two optionally substituted $C_1$-$C_{15}$ alkyl groups; the linker not comprising any nitro, nitroso or peroxy groups.

If the heterocycles or aromatic nuclei are substituted, they may be substituted, for example, with at least one $C_1$-$C_8$ alkyl radical optionally substituted with a hydroxyl, $C_1$-$C_2$ alkoxy, $C_2$-$C_4$ hydroxyalkoxy, acetylamino, or amino group substituted with one or two $C_1$-$C_4$ alkyl radicals, optionally bearing at least one hydroxyl group, or the two radicals possibly forming, with the nitrogen atom to which they are attached, a 5- or 6-membered heterocycle optionally comprising another heteroatom identical to or different from nitrogen; a halogen atom; a hydroxyl group; a $C_1$-$C_2$ alkoxy radical; a $C_2$-$C_4$ hydroxyalkoxy radical; an amino radical; an amino radical substituted with one or two identical or different $C_1$-$C_4$ alkyl radicals optionally bearing at least one hydroxyl group.

Among the benzenic direct dyes that may be used, mention may be made in a nonlimiting manner of the following compounds:
1,4-diamino-2-nitrobenzene,
1-amino-2-nitro-4-p-hydroxyethylaminobenzene,
1-amino-2-nitro-4-bis(p-hydroxyethyl)aminobenzene,
1,4-bis(p-hydroxyethylamino)-2-nitrobenzene,
1-β-hydroxyethylamino-2-nitro-4-bis(β-hydroxyethylamino)benzene,
1-β-hydroxyethylamino-2-nitro-4-aminobenzene,
1-β-hydroxyethylamino-2-nitro-4-(ethyl)(β-hydroxyethyl)aminobenzene,
1-amino-3-methyl-4-β-hydroxyethylamino-6-nitrobenzene,
1-amino-2-nitro-4-β-hydroxyethylamino-5-chlorobenzene,
1,2-diamino-4-nitrobenzene,
1-amino-2-β-hydroxyethylamino-5-nitrobenzene,
1,2-bis(β-hydroxyethylamino)-4-nitrobenzene,
1-amino-2-tris(hydroxymethyl)methylamino-5-nitrobenzene,
1-hydroxy-2-amino-5-nitrobenzene,
1-hydroxy-2-amino-4-nitrobenzene,
1-hydroxy-3-nitro-4-aminobenzene,
1-hydroxy-2-amino-4,6-dinitrobenzene,
1-β-hydroxyethyloxy-2-β-hydroxyethylamino-5-nitrobenzene,
1-methoxy-2-β-hydroxyethylamino-5-nitrobenzene,
1-β-hydroxyethyloxy-3-methylamino-4-nitrobenzene,
1-β,γ-dihydroxypropyloxy-3-methylamino-4-nitrobenzene,
1-β-hydroxyethylamino-4-β,γ-dihydroxypropyloxy-2-nitrobenzene,
1-β,γ-dihydroxypropylamino-4-trifluoromethyl-2-nitrobenzene,
1-β-hydroxyethylamino-4-trifluoromethyl-2-nitrobenzene,
1-β-hydroxyethylamino-3-methyl-2-nitrobenzene,
1-β-aminoethylamino-5-methoxy-2-nitrobenzene,
1-hydroxy-2-chloro-6-ethylamino-4-nitrobenzene,
1-hydroxy-2-chloro-6-amino-4-nitrobenzene,
1-hydroxy-6-bis(β-hydroxyethyl)amino-3-nitrobenzene,
1-β-hydroxyethylamino-2-nitrobenzene, and
1-hydroxy-4-β-hydroxyethylamino-3-nitrobenzene.

Among the azo, azomethine, methine and tetraazapentamethine direct dyes that may be used in the process described herein, non-limiting mention may be made of the cationic dyes described in patent applications WO 95/15144, WO 95/01772 and EP 714 954; FR 2 189 006, FR 2 285 851, FR 2 140 205, EP 1 378 544 and EP 1 674 073.

Thus, non-limiting mention may be made for example of the following dyes of formulae (I) to (IV), and for example those of formulae (I) and (III):

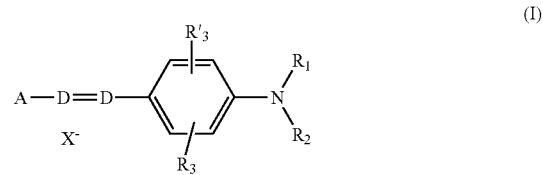

(I)

wherein:
D represents a nitrogen atom or a —CH group,
$R_1$ and $R_2$, which may be identical or different, represent a hydrogen atom; a $C_1$-$C_4$ alkyl radical which may be substituted with a —CN, —OH or —NH$_2$ radical, or form, with a carbon atom of the benzene ring, a heterocycle optionally containing oxygen or nitrogen, which may be substituted with at least one $C_1$-$C_4$ alkyl radical; a 4'-aminophenyl radical, $R_3$ and $R'_3$, which may be identical or different, represent a hydrogen atom or a halogen atom chosen from chlorine, bromine, iodine and fluorine, or a cyano, $C_1$-$C_4$ alkyl, $C_1$-$C_4$ alkoxy or acetyloxy radical, $X^-$ represents an anion for example chosen from chloride, methyl sulfate and acetate, A represents a group chosen from structures $A_1$ to $A_{18}$ below:

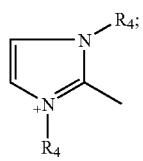
$A_1$

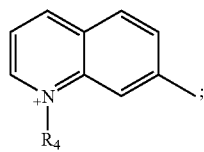
$A_2$

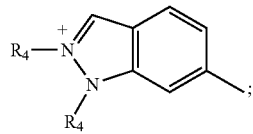
$A_3$

$A_4$

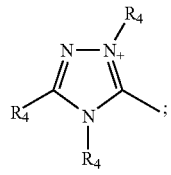
$A_5$

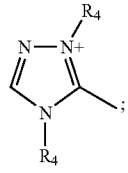
$A_6$

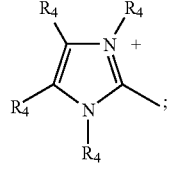
$A_7$

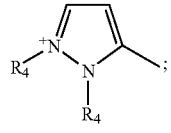
$A_8$

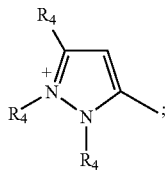
$A_9$

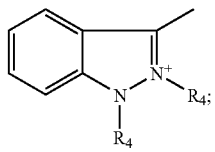
$A_{10}$

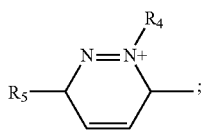
$A_{11}$

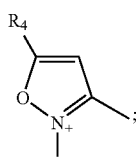
$A_{12}$

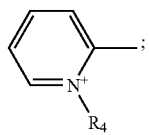
$A_{13}$

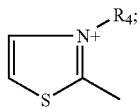
$A_{14}$

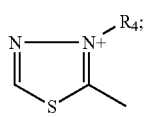
$A_{15}$

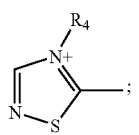
$A_{16}$

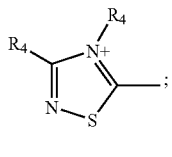
$A_{17}$

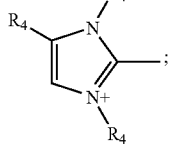
$A_{18}$ wherein $R_4$ represents a $C_1$-$C_4$ alkyl radical which may be substituted with a hydroxyl radical and $R_5$ represents a $C_1$-$C_4$ alkoxy radical;

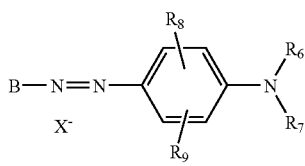

(II)

wherein:

R$_6$ represents a hydrogen atom or a C$_1$-C$_4$ alkyl radical,

R$_7$ represents a hydrogen atom, an alkyl radical which may be substituted with a —CN radical or with an amino group, a 4'-aminophenyl radical, or forms with R$_6$ a heterocycle optionally containing oxygen and/or nitrogen, which may be substituted with a C$_1$-C$_4$ alkyl radical, R$_8$ and R$_9$, which may be identical or different, represent a hydrogen atom, a halogen atom such as bromine, chlorine, iodine or fluorine, a C$_1$-C$_4$ alkyl or C$_1$-C$_4$ alkoxy radical, or a —CN radical, X$^-$ represents an anion for example chosen from chloride, methyl sulfate and acetate, B represents a group chosen from structures B1 to B6 below:

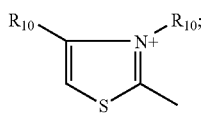

B1

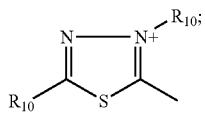

B2

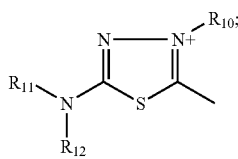

B3

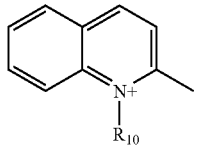

B4

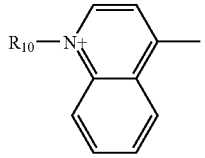

B5

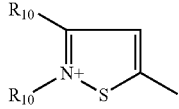

B6 wherein R$_{10}$ represents a C$_1$-C$_4$ alkyl radical, R$_{11}$ and R$_{12}$, which may be identical or different, represent a hydrogen atom or a C$_1$-C$_4$ alkyl radical;

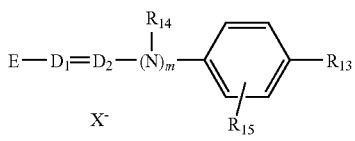

(III)

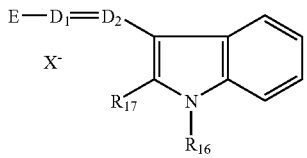

(III')

wherein:

R$_{13}$ represents a hydrogen atom, a C$_1$-C$_4$ alkoxy radical or a halogen atom such as bromine, chlorine, iodine or fluorine, R$_{14}$ represents a hydrogen atom, a C$_1$-C$_4$ alkyl radical or forms, with a carbon atom of the benzene ring, a heterocycle optionally containing oxygen and/or substituted with one or more C$_1$-C$_4$ alkyl groups, R$_{15}$ represents a hydrogen atom or a halogen atom such as bromine, chlorine, iodine or fluorine, R$_{16}$ and R$_{17}$, which may be identical or different, represent a hydrogen atom or a C$_1$-C$_4$ alkyl radical, D$_1$ and D$_2$, which may be identical or different, represent a hydrogen atom or a —CH group, m=0 or 1, such as 1, it being understood that when R$_{13}$ represents an unsubstituted amino group, then D$_1$ and D$_2$ simultaneously represent a —CH group and m=0, X$^-$ represents an anion for example chosen from chloride, methyl sulfate and acetate, E represents a group chosen from structures E1 to E8 below, such as E1, E2 and E7:

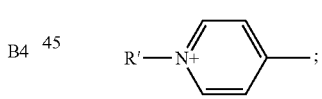

E1

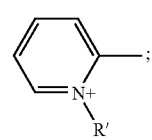

E2

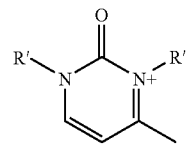

E3

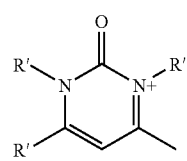

E4

-continued

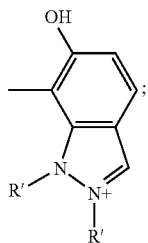
E5

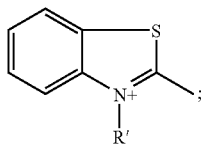
E6

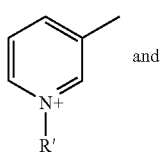  and
E7

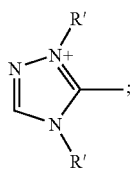
E8 wherein R' represents a $C_1$-$C_4$ alkyl radical;

when m=0 and $D_1$ represents a nitrogen atom, then E may also denote a group of structure E9 below:

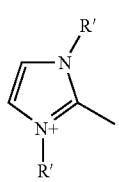
E9 wherein R' represents a $C_1$-$C_4$ alkyl radical.

$$G-N=N-J \quad (IV)$$

wherein:

the symbol G represents a group chosen from the structures $G_1$ to $G_3$ below:

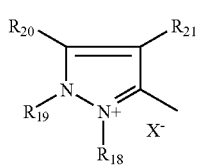
$G_1$

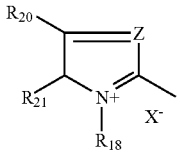
$G_2$

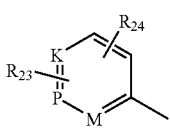
$G_3$ wherein structures $G_1$ to $G_3$:

$R_{18}$ denotes a $C_1$-$C_4$ alkyl radical, a phenyl radical which may be substituted with a $C_1$-$C_4$ alkyl radical, or a halogen atom chosen from chlorine, bromine, iodine and fluorine;

$R_{19}$ denotes a $C_1$-$C_4$ alkyl radical or a phenyl radical;

$R_{20}$ and $R_{21}$, which may be identical or different, represent a $C_1$-$C_4$ alkyl radical, a phenyl radical, or form together in $G_1$ a benzene ring substituted with at least one $C_1$-$C_4$ alkyl, $C_1$-$C_4$ alkoxy or $NO_2$ radicals, or form together in $G_2$ a benzene ring optionally substituted with at least one $C_1$-$C_4$ alkyl, $C_1$-$C_4$ alkoxy or $NO_2$ radicals;

$R_{20}$ may also denote a hydrogen atom;

Z represents an oxygen or sulfur atom or a group —$NR_{19}$,

M represents a group —CH, —CR(R denoting $C_1$-$C_4$ alkyl) or —$NR_{22}(C)_r$;

K represents a group —CH, —CR(R denoting $C_1$-$C_4$ alkyl) or —$NR_{22}(X^{-x})_r$;

P represents a group —CH, —CR(R denoting $C_1$-$C_4$ alkyl) or —$NR_{22}(X^-)_r$;

r denotes 0 or 1;

$R_{22}$ represents an $O^-$ atom, a $C_1$-$C_4$ alkoxy radical or a $C_1$-$C_4$ alkyl radical;

$R_{23}$ and $R_{24}$, which may be identical or different, represent a hydrogen atom or a halogen atom chosen from chlorine, bromine, iodine and fluorine, a $C_1$-$C_4$ alkyl or $C_1$-$C_4$ alkoxy radical, or an —$NO_2$ radical;

$X^-$ represents an anion for example chosen from chloride, iodide, methyl sulfate, ethyl sulfate, acetate and perchlorate;

with the proviso that, if $R_{22}$ denotes $O^-$, then r denotes zero;

if K or P or M denotes —N—$(C_1$-$C_4)$alkyl $X^-$, then $R_{23}$ or $R_{24}$ is for example other than a hydrogen atom;

if K denotes —$NR_{22}(X^-)_r$, then M=P—CH, —CR;

if M denotes —$NR_{22}(X^-)_r$, then K=P—CH, —CR;

if P denotes —$NR_{22}(X^-)_r$, then K=M and denote —CH or —CR;

if Z denotes a sulfur atom with $R_{21}$ denoting $C_1$-$C_4$ alkyl, then $R_{20}$ is other than a hydrogen atom;

if Z denotes —$NR_{22}$ with $R_{19}$ denoting $C_1$-$C_4$ alkyl, then at least one of the radicals $R_{18}$, $R_{20}$ or $R_{21}$ of the group of structure $G_2$ is other than a $C_1$-$C_4$ alkyl radical;

the symbol J represents:

(a) a group of structure $J_1$ below:

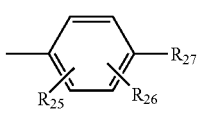
$J_1$ wherein structure $J_1$:

$R_{25}$ represents a hydrogen atom, a halogen atom chosen from chlorine, bromine, iodine and fluorine, a $C_1$-$C_4$ alkyl or $C_1$-$C_4$ alkoxy radical, an —OH, —$NO_2$, —$NHR_{28}$, —$NR_{29}R_{30}$ or $C_1$-$C_4$—NHCOalkyl radical, or forms with $R_{26}$ a 5- or 6-membered ring optionally containing one or more heteroatoms chosen from nitrogen, oxygen and sulfur;

$R_{26}$ represents a hydrogen atom, a halogen atom chosen from chlorine, bromine, iodine and fluorine, a $C_1$-$C_4$ alkyl or $C_1$-$C_4$ alkoxy radical, or forms with $R_{27}$ or $R_{28}$ a 5- or 6-membered ring optionally containing one or more heteroatoms chosen from nitrogen, oxygen and sulfur;

$R_{27}$ represents a hydrogen atom, an —OH radical, a radical —$NHR_{28}$ or a radical —$NR_{29}R_{30}$;

$R_{28}$ represents a hydrogen atom, a $C_1$-$C_4$ alkyl radical, a $C_1$-$C_4$ monohydroxyalkyl, $C_2$-$C_4$ polyhydroxyalkyl radical or a phenyl radical;

$R_{29}$ and $R_{30}$, which may be identical or different, represent a $C_1$-$C_4$ alkyl radical, a $C_1$-$C_4$ monohydroxyalkyl or $C_2$-$C_4$ polyhydroxyalkyl radical;

(b) a 5- or 6-membered nitrogenous heterocyclic group, which may contain other heteroatoms and/or carbonyl groups and may be substituted with at least one $C_1$-$C_4$ alkyl, amino or phenyl radical, and for example a group of structure $J_2$ below:

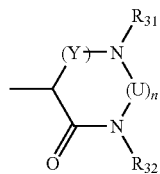

wherein structure $J_2$:

$R_{31}$ and $R_{32}$, which may be identical or different, represent a hydrogen atom, a $C_1$-$C_4$ alkyl radical or a phenyl radical;

Y denotes a —CO— radical or a

radical;

n=0 or 1, with, when n denotes 1, U denoting a —CO— radical.

In structures (I) to (IV) defined above, the $C_1$-$C_4$ alkyl or alkoxy group may for example denote methyl, ethyl, butyl, methoxy or ethoxy.

In certain embodiments, A represents a group chosen from structures $A_1$, $A_4$, $A_7$, $A_{13}$ and $A_{18}$.

Among the compounds of formulae (I) and (III), the following compounds may for example be used:

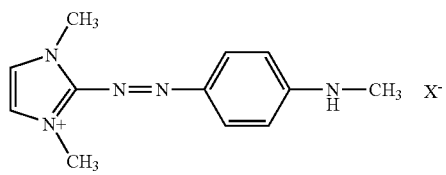

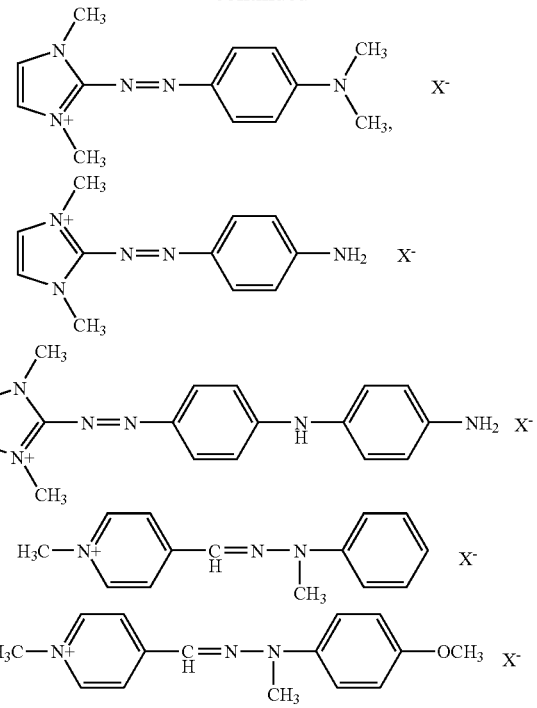

Among the azo direct dyes that may also be mentioned in a non-limiting manner are the following dyes, described in the Color Index International, 3rd edition:
Disperse Red 17
Basic Red 22
Basic Red 76
Basic Yellow 57
Basic Brown 16
Basic Brown 17
Disperse Black 9.

Non-limiting mention may also be made of 1-(4'-aminodiphenylazo)-2-methyl-4-bis(β-hydroxyethyl)aminobenzene.

Among the quinone direct dyes that may be mentioned in a non-limiting manner are the following dyes:
Disperse Red 15
Solvent Violet 13
Disperse Violet 1
Disperse Violet 4
Disperse Blue 1
Disperse Violet 8
Disperse Blue 3
Disperse Red 11
Disperse Blue 7
Basic Blue 22
Disperse Violet 15
Basic Blue 99
and also the following compounds:
1-N-methylmorpholiniumpropylamino-4-hydroxyanthraquinone
1-aminopropylamino-4-methylaminoanthraquinone
1-aminopropylaminoanthraquinone
5-β-hydroxyethyl-1,4-diaminoanthraquinone
2-aminoethylaminoanthraquinone
1,4-bis(β,γ-dihydroxypropylamino)anthraquinone.

Among the azine dyes that may be mentioned in a non-limiting manner are the following compounds:

Basic Blue 17

Basic Red 2.

Among the triarylmethane dyes that may be used in the process described herein, non-limiting mention may be made of the following compounds:

Basic Green 1

Basic Violet 3

Basic Violet 14

Basic Blue 7

Basic Blue 26.

Among the indoamine dyes that may be used in the process described herein, non-limiting mention may be made of the following compounds:

2-β-hydroxyethylamino-5-[bis(β-4'-hydroxyethyl)amino] anilino-1,4-benzoquinone

2-β-hydroxyethylamino-5-(2'-methoxy-4'-amino)anilino-1,4-benzoquinone

3-N-(2'-chloro-4'-hydroxy)phenylacetylamino-6-methoxy-1,4-benzoquinone imine

3-N-(3'-chloro-4'-methylamino)phenylureido-6-methyl-1,4-benzoquinone imine

3-[4'-N-(ethyl, carbamylmethyl)amino]phenylureido-6-methyl-1,4-benzoquinone imine.

Among the dyes of tetraazapentamethine type that may be used, non-limiting mention may be made of the following compounds given in the table below:

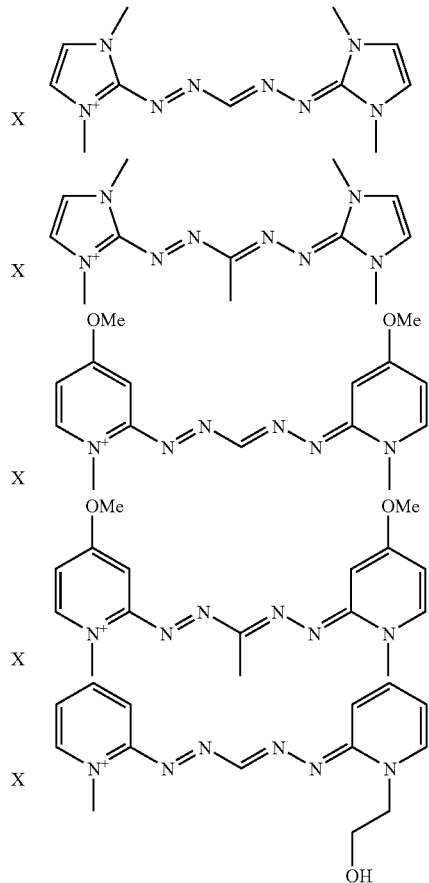

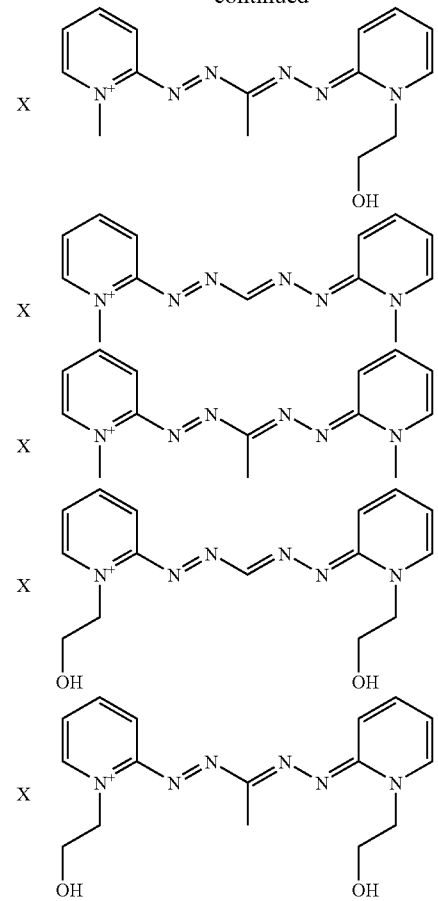

X⁻ represents an anion for example chosen from chloride, iodide, methyl sulfate, ethyl sulfate, acetate, and perchlorate.

Among the polychromophoric dyes, non-limiting mention may be made for example of symmetrical or non-symmetrical azo and/or azomethine (hydrazone) di- or trichromophoric dyes comprising, on the one hand, at least one optionally fused 5- or 6-membered aromatic heterocycle, comprising at least one quaternized nitrogen atom engaged in the said heterocycle and optionally at least one other heteroatom (such as nitrogen, sulfur or oxygen), and, on the other hand, at least one optionally substituted phenyl or naphthyl group, optionally bearing at least one group OR with R representing a hydrogen atom, an optionally substituted $C_1$-$C_6$ alkyl radical, an optionally substituted phenyl nucleus, or at least one group $N(R')_2$ with R', which may be identical or different, representing a hydrogen atom, an optionally substituted $C_1$-$C_6$ alkyl radical or an optionally substituted phenyl nucleus; the radicals R' possibly forming, with the nitrogen atom to which they are attached, a saturated 5- or 6-membered heterocycle, or alternatively one and/or both the radicals R' may each form, with the carbon atom of the aromatic ring located ortho to the nitrogen atom, a saturated 5- or 6-membered heterocycle.

Aromatic cationic heterocycles that may for example be mentioned in a non-limiting manner include 5- or 6-membered rings containing 1 to 3 nitrogen atoms and for example 1 or 2 nitrogen atoms, one being quaternized; the said heterocycle moreover being optionally fused to a benzene nucleus. It should similarly be noted that the heterocycle may optionally comprise another heteroatom other than nitrogen, for instance sulfur or oxygen.

If the heterocycles or phenyl or naphthyl groups are substituted, in some embodiments, they may be substituted, for example, with at least one $C_1$-$C_4$ alkyl radical optionally substituted with a hydroxyl, $C_1$-$C_2$ alkoxy, $C_2$-$C_4$ hydroxyalkoxy, acetylamino or amino group substituted with one or two $C_1$-$C_4$ alkyl radicals optionally bearing at least one hydroxyl group, or the two radicals possibly forming, with the nitrogen atom to which they are attached, a 5- or 6-membered heterocycle, optionally comprising another heteroatom identical to or different from nitrogen; a halogen atom; a hydroxyl group; a $C_1$-$C_2$ alkoxy radical; a $C_2$-$C_4$ hydroxyalkoxy radical; an amino radical; an amino radical substituted with one or two identical or different $C_1$-$C_4$ alkyl radicals, optionally bearing at least one hydroxyl group.

These polychromophores may be connected together by means of at least one linker optionally comprising at least one quaternized nitrogen atom that may or may not be engaged in a saturated or unsaturated, optionally aromatic heterocycle.

In some embodiments, the linker may be a linear, branched or cyclic $C_1$-$C_{20}$ alkyl chain, optionally interrupted with at least one heteroatom (such as nitrogen or oxygen) and/or with at least one group comprising such a heteroatom (CO or $SO_2$), optionally interrupted with at least one heterocycle that may or may not be fused to a phenyl nucleus and comprising at least one quaternized nitrogen atom engaged in the said ring and optionally at least one other heteroatom (such as oxygen, nitrogen or sulfur), optionally interrupted with at least one substituted or unsubstituted phenyl or naphthyl group, optionally at least one quaternary ammonium group substituted with two optionally substituted $C_1$-$C_{15}$ alkyl groups; the linker not comprising any nitro, nitroso or peroxy groups.

In some embodiments, the bonding between the linker and each chromophore may take place via a heteroatom substituent on the phenyl or naphthyl nucleus or via the quaternized nitrogen atom of the cationic heterocycle.

The dye may comprise identical or different chromophores.

As examples of such dyes, non-limiting reference may be made for example to patent applications EP 1 637 566, EP 1 619 221, EP 1 634 926, EP 1 619 220, EP 1 672 033, EP 1 671 954, EP 1 671 955, EP 1 679 312, EP 1 671 951, EP 167 952, EP 167 971, WO 06/063 866, WO 06/063 867, WO 06/063 868, WO 06/063 869, EP 1 408 919, EP 1 377 264, EP 1 377 262, EP 1 377 261, EP 1 377 263, EP 1 399 425, EP 1 399 117, EP 1 416 909, EP 1 399 116 and EP 1 671 560.

In some embodiments, it may also be possible to use the cationic direct dyes mentioned for example in patent applications: EP 1 006 153, which describes dyes comprising two chromophores of anthraquinone type connected via a linker of cationic type; EP 1 433 472, EP 1 433 474, EP 1 433 471 and EP 1 433 473, which describe identical or different dichromophoric dyes, connected via a cationic or non-cationic linker, and also EP 6 291 333, which for example describes dyes comprising three chromophores, one of them being an anthraquinone chromophore, to which are attached two chromophores of azo or diazacarbocyanin type or an isomer thereof.

Among the natural direct dyes that may be used, non-limiting mention may be made of lawsone, juglone, alizarin, purpurin, carminic acid, kermesic acid, purpurogallin, protocatechaldehyde, indigo, isatin, curcumin, spinulosin, apigenidin and orceins. It may also be possible to use extracts or decoctions comprising these natural dyes and for example henna-based poultices or extracts.

When present, the at least one direct dye may be present in an amount ranging from 0.0001% to 10% by weight, such as from 0.005% to 5% by weight, relative to the total weight of the at least one composition (B).

In some embodiments, the at least one composition (B) used in the dyeing process may comprise one and/or the other type of dye, and may optionally correspond to two dye compositions, one comprising the at least one oxidation dye, the other the at least one direct dye.

In some embodiments, the at least one composition (B) used in the dyeing process or in the lightening process may be an aqueous or non-aqueous composition. As used herein, the term "aqueous composition" means a composition comprising more than 5% by weight of water, for example more than 10% by weight of water, such as more than 20% by weight of water.

In some embodiments, the at least one composition (B) may be an aqueous composition.

In some embodiments, the at least one composition (B) may optionally comprise at least one organic solvent. Non-limiting examples of the at least one organic solvent that may be mentioned include $C_2$-$C_4$ linear or branched alkanols, such as ethanol and isopropanol; glycerol; polyols and polyol ethers, for instance 2-butoxyethanol, propylene glycol, dipropylene glycol, propylene glycol monomethyl ether, and diethylene glycol monomethyl ether and monoethyl ether, and also aromatic alcohols such as benzyl alcohol or phenoxyethanol, and mixtures thereof.

In some embodiments, the at least one organic solvent, if present, may be present in an amount ranging from 1% to 40% by weight, such as from 5% to 30% by weight, relative to the weight of the at least one composition (B).

In some embodiments, the at least one composition (B) may also contain various adjuvants such as those mentioned for example in the context of composition (A), such as anionic, cationic, nonionic, amphoteric or zwitterionic surfactants or mixtures thereof, anionic, cationic, nonionic, amphoteric or zwitterionic polymers or mixtures thereof; mineral thickeners, for instance fillers such as clays, talc; organic thickeners with, for example, anionic, cationic, nonionic and amphoteric polymeric associative thickeners; antioxidants; penetrants; sequestrants; fragrances; dispersants; film-forming agents; conditioning agents; ceramides; preserving agents; opacifiers.

The above adjuvants may each for example be present in an amount ranging from 0.01% to 20% by weight, relative to the weight of the at least one composition (A).

The at least one composition (A) may also comprise at least one organic thickener.

The at least one organic thickener may be chosen from fatty acid amides (coconut monoethanolamide or diethanolamide, oxyethylenated alkyl ether carboxylic acid monoethanolamide), polymeric thickeners such as cellulose-based thickeners (hydroxyethylcellulose, hydroxypropylcellulose or carboxymethylcellulose), guar gum and derivatives thereof (hydroxypropyl guar), gums of microbial origin (xanthan gum, scleroglucan gum), acrylic acid or acrylamidopropanesulfonic acid crosslinked homopolymers and associative polymers (polymers comprising hydrophilic regions and fatty-chain hydrophobic regions (alkyl or alkenyl containing at least 10 carbon atoms) that are capable, in an aqueous medium, of reversibly combining with each other or with other molecules).

In some embodiments, the at least one organic thickener may be chosen from cellulose-based thickeners (hydroxyethylcellulose, hydroxypropylcellulose or carboxymethylcellulose), guar gum and derivatives thereof (hydroxypropyl guar), gums of microbial origin (xanthan gum, scleroglucan gum) and acrylic acid or acrylamidopropanesulfonic acid crosslinked homopolymers, and for example from cellulose-based thickeners such as with hydroxyethylcellulose.

The at least one organic thickener, if present, may be present in an amount ranging from 0.01% to 20% by weight, such as from 0.1% to 5% by weight, relative to the weight of the at least one composition (A).

The process described herein is performed with at least one composition (C) comprising at least one oxidizing agent.

In some embodiments, the at least one oxidizing agent may be chosen from hydrogen peroxide, urea peroxide, alkali metal bromates or ferricyanides, and peroxygenated salts, for instance alkali metal or alkaline-earth metal persulfates, perborates or percarbonates, and also peracids, and precursors thereof.

The at least one oxidizing agent may for example be constituted by hydrogen peroxide, for instance as an aqueous solution (aqueous hydrogen peroxide solution), wherein the at least one oxidizing agent may be present in an amount ranging, for instance, from 0.1% to 50% by weight, for example from 0.5% to 20% by weight, such as from 1% to 15% by weight, relative to the weight of the oxidizing composition.

As a function of the desired degree of lightening, the at least one oxidizing agent may also comprise at least one oxidizing agent for example chosen from peroxygenated salts.

In some embodiments, when the process described herein is a dyeing process, then the at least one oxidizing agent is not chosen from peroxygenated salts, peracids, and the precursors thereof.

The at least one composition (C) may be aqueous or non-aqueous. As used herein, the term "aqueous composition" means a composition comprising water present in an amount of greater than 5% by weight, for example greater than 10% by weight, such as greater than 20% by weight, relative to the weight of the composition.

In some embodiments, the at least one composition (C) may be an aqueous composition.

In some embodiments, it may also comprise at least one organic solvent.

Non-limiting examples of the at least one organic solvent that may be mentioned include linear or branched $C_2$-$C_4$ alkanols, such as ethanol and isopropanol; glycerol; polyols and polyol ethers, for instance 2-butoxyethanol, propylene glycol, dipropylene glycol, propylene glycol monomethyl ether, diethylene glycol monomethyl ether and monoethyl ether, and also aromatic alcohols, for instance benzyl alcohol or phenoxyethanol, and mixtures thereof.

When present, the at least one organic solvent may be present in an amount ranging from 1% to 40% by weight, such as from 5% to 30% by weight, relative to the weight of the at least one composition (C).

In some embodiments, the at least one composition (C) may comprise at least one acidifying agent.

Non-limiting examples of acidifying agents that may be mentioned include mineral or organic acids, for instance hydrochloric acid, orthophosphoric acid, sulfuric acid, carboxylic acids, for instance acetic acid, tartaric acid, citric acid or lactic acid, and sulfonic acids.

In some embodiments, the pH of the at least one composition (C), when it is aqueous, may be less than 7.

In some embodiments, the at least one composition (C) may also contain other ingredients conventionally used in the field, such as those detailed previously in the context of the at least one compositions (A) and (B).

In some embodiments, the at least one oxidizing composition (C) may be in various forms, for instance a solution, an emulsion, or a gel.

In some embodiments of the process described herein, the process for dyeing or lightening human keratin fibers comprises applying to the keratin fibers a cosmetic composition comprising:

a) at least one anhydrous composition (A) comprising at least one fatty substance and at least one surfactant;

b) at least one composition (B) comprising monoethanolamine and at least one basic amino acid; and c) at least one composition (C) comprising at least one oxidizing agent;

provided that when the process is a dyeing process, the at least one anhydrous composition (A) is free from organic amines and the at least one composition (B) comprises at least one oxidation dye and/or at least one direct dye;

wherein applying to the keratin fibers comprises:

mixing, at the time of use, the at least one anhydrous composition (A), the at least one composition (B), and the at least one composition (C); and applying the resultant composition to the keratin fibers.

In some embodiments, the weight ratios R1 of the amounts of compositions [(A)+(B)]/(C) and R2 of the amounts of compositions (A)/(B) may range from 0.1 to 10, such as from 0.3 to 3.

In some embodiments, when the process is a dyeing process, then the weight ratio R1 (A)+(B)/(C) may range from 0.5 to 1.

In some embodiments, compositions (A), (B) and (C) may be applied to wet or dry keratin fibers, successively and without intermediate rinsing.

In some embodiments, for example, the at least one anhydrous composition (A), then the at least one composition (B) and then the at least one composition (C); or the at least one composition (B), then the at least one anhydrous composition (A) and then the at least one composition (C) may be applied.

In some embodiments, the at least one composition (C), and then the mixture resulting from compositions (A) and (B) may also be applied successively and without intermediate rinsing. Thus, also provided is a process for dyeing or lightening human keratin fibers, comprising applying to the keratin fibers a cosmetic composition comprising:

a) at least one anhydrous composition (A) comprising at least one fatty substance and at least one surfactant;

b) at least one composition (B) comprising monoethanolamine and at least one basic amino acid; and c) at least one composition (C) comprising at least one oxidizing agent;

provided that when the process is a dyeing process, the at least one anhydrous composition (A) is free from organic amines and the at least one composition (B) comprises at least one oxidation dye and/or at least one direct dye;

wherein applying to the keratin fibers comprises:

applying to the keratin fibers the at least one composition (C);

mixing, at the time of use, the at least one anhydrous composition (A) and the at least one composition (B) to form a resultant mixture, and applying the resultant mixture to the keratin fibers;

wherein the at least one composition (C) and the resultant mixture are applied to the keratin fibers, successively and without intermediate rinsing.

In some embodiments, the weight ratios R1 of the amounts of compositions [(A)+(B)]/(C) and R2 of the amounts of compositions (A)/(B) may range for example from 0.1 to 10, such as from 0.3 to 3.

In addition, the mixture applied to the fibers (resulting either from the extemporaneous mixing of compositions (A), (B) and (C) or from their partial or total successive application) may be left in place for a period of time ranging, from example, from 1 minute to 1 hour, such as from 5 minutes to 30 minutes.

The temperature during the process may for example range from room temperature (for instance from 15 to 25° C.) to 80° C., such as from room temperature to 60° C.

After the treatment, the human keratin fibers may optionally be rinsed with water, optionally washed with a shampoo followed by rinsing with water, and then dried or left to dry.

In some embodiments, if the cosmetic composition applied to the hair (comprising compositions (A), (B) and (C)) comprises aqueous ammonia or a salt thereof, its content may be less than or equal to 0.03% by weight of the final composition (expressed as $NH_3$) and for example less than or equal to 0.01% by weight relative to the final composition. The final composition results from the mixing of compositions (A), (B) and (C); this mixing being performed either before application to the keratin fibers (extemporaneous preparation) or directly on the keratin fibers (successive applications with or without premixing and without intermediate rinsing). In some embodiments, if the composition comprises aqueous ammonia or a salt thereof, then the amount of basifying agent(s) is greater than that of the aqueous ammonia (expressed as $NH_3$).

However, in some embodiments, compositions (A), (B) and (C) for example do not comprise aqueous ammonia.

According to one variant, the composition according to the process described herein obtained after mixing together the compositions (A), (B) and (C) described previously is such that, after mixing, the at least one fatty substance is present in an amount of greater than 20% by weight, for example greater than 25% by weight, such as greater than 30% by weight, relative to the weight of the final composition.

Also provided is a multi-compartment device comprising:

a first compartment comprising at least one an anhydrous composition (A) comprising at least one fatty substance and at least one surfactant;

a second compartment comprising at least composition (B) comprising monoethanolamine and at least one basic amino acid; and a third compartment comprising at least one composition (C) comprising at least one oxidizing agent.

The examples that follow serve to illustrate the process described herein without, however, being limiting in nature.

EXAMPLES

Dyeing Example 1

The following compositions were prepared (unless otherwise indicated, the amounts are expressed in g %):
Composition A

| | |
|---|---|
| Oxyethylenated (4 EO) sorbitan monolaurate | 21.67 |
| Fumed silica of hydrophobic nature | 11 |
| Liquid petroleum jelly | qs 100 |

Composition B1

| | |
|---|---|
| para-Phenylenediamine | 6.55 |
| Resorcinol | 4.95 |
| 2-Methylresorcinol | 1.86 |
| 2,4-Diaminophenoxyethanol HCl | 0.15 |
| Sodium metabisulfite | 0.45 |
| Erythorbic acid | 0.31 |
| Pure monoethanolamine | 40.07 |
| Arginine | 7.00 |
| Water | qs 100 |

At the time of use, the following were mixed together:

10 parts by weight of composition A;

4 parts by weight of composition B1; and 15 parts by weight of Platinium international 20-volumes oxidizing agent (amount of hydrogen peroxide: 6% by weight).

The mixture was then applied to a lock of natural hair containing 90% grey hairs (NG) and to a lock of permanent-waved hair containing 90% grey hairs (PWG).

The "mixture/lock" bath ratio was, respectively, 10/1 (g/g).

The leave-on time was 30 minutes at 27° C.

After the leave-on time, the locks were rinsed, and then washed with Elvive multivitamin shampoo, and dried.

The inventive composition gave a powerful, sparingly selective matte effect.

Dyeing Example 2

The following compositions were prepared (unless otherwise indicated, the amounts are expressed in g %):
Composition A

| | |
|---|---|
| Oxyethylenated (4 EO) sorbitan monolaurate | 21.67 |
| Fumed silica of hydrophobic nature | 11 |
| Liquid petroleum jelly | qs 100 |

Composition B1

| | |
|---|---|
| 1-Hydroxy-4-aminobenzene | 3.27 |
| 2-Amino-3-hydroxypyridine | 3.30 |
| Sodium metabisulfite | 0.45 |
| Erythorbic acid | 0.31 |
| Pure monoethanolamine | 40.0 |
| Arginine | 7.00 |
| Oleyl alcohol polyglycerolated with 2 mol of glycerol | 2.1 |
| Oleyl alcohol polyglycerolated with 4 mol of glycerol | 3.0 AM |
| Oleic acid | 1.58 |
| Oleylamine containing 2 mol of ethylene oxide, sold under the trade name Ethomeen 012 by the company Akzo | 3.69 |
| Dimethylaminopropyl laurylaminosuccinamate, sodium salt, at 55% AM | 1.58 AM |
| Oleyl alcohol | 2.64 |
| Oleic acid diethanolamide | 6.32 |
| Ethyl alcohol | 3.69 |
| Propylene glycol | 1.84 |
| Dipropylene glycol | 0.26 |
| Propylene glycol monomethyl ether | 4.74 |
| Demineralized water qs | qs 100 |

AM: active material

At the time of use, the following were mixed together:

10 parts by weight of composition A;

4 parts by weight of composition B1; and parts by weight of Platinium international 20-volumes oxidizing agent (amount of hydrogen peroxide: 6% by weight).

The mixture was then applied to a lock of natural hair containing 90% grey hairs (NG) and to a lock of permanent-waved hair containing 90% grey hairs (PWG).

The "mixture/lock" bath ratio was, respectively, 10/1 (g/g). The leave-on time was 30 minutes at 27° C.

After the leave-on time, the locks were rinsed, and then washed with Elvive multivitamin shampoo, and dried.

The inventive composition gave a strong coppery, sparingly selective dyeing result.

Lightening Example 3

The following compositions were prepared (unless otherwise indicated, the amounts are expressed in g %):

Composition A

| | |
|---|---|
| Oxyethylenated (4 EO) sorbitan monolaurate | 21.67 |
| Fumed silica of hydrophobic nature | 11 |
| Liquid petroleum jelly | qs 100 |

Compositions B1 and B2

| | Composition B1 (inventive) | Composition B2 (comparative) |
|---|---|---|
| L-Arginine | 7 | — |
| Monoethanolamine | 14.5 | 14.5 |
| Hexylene glycol | 3 | 3 |
| Dipropylene glycol | 3 | 3 |
| Denatured ethyl alcohol | 8.8 | 8.8 |
| Propylene glycol | 6.2 | 6.2 |
| Hydroxyethylcellulose (MW = 1 300 000) | 1.5 | 1.5 |
| L-Ascorbic acid | 0.25 | 0.25 |
| Pentasodium pentetate | 1 | 1 |
| Sodium metabisulfite | 0.7 | 0.7 |
| Demineralized water | qs 100 g | qs 100 g |

At the time of use, the following were mixed together:

10 parts by weight of composition A:

4 parts by weight of composition B1 or of composition B2; and 15 parts by weight of Platinium international 20-volumes oxidizing agent (amount of hydrogen peroxide: 6% by weight).

The mixture was then applied to a lock of natural hair (tone depth: 4).

The "mixture/lock" bath ratio was, respectively, 10/1 (g/g). The leave-on time was 30 minutes at 27° C.

After the leave-on time, the locks were rinsed, and then washed with Elvive multivitamin shampoo, and dried.

Results

The pH of the mixtures obtained with composition B1 was identical to that obtained with composition B2, i.e. pH=9.9.

The coloration of the locks was measured in the CIE L*a*b* system using a Minolta CM2600d colorimeter in the CIE L a b system (illuminant: D65, angle 10°, specular components included).

The lightening was evaluated by calculating the value of $\Delta E^*ab$ according to the following formula:

$$\Delta E^*ab = [(L^*_0 - L^*_1)^2 + (a^*_0 - a^*_1)^2 + (b^*_0 - b^*_1)^2]^{1/2}$$

in which $L^*_0$, $a^*_0$ and $b^*_0$ are the L a b coefficients of the untreated lock and $L^*_1$, $a^*_1$ and $b^*_1$ are the L a b coefficients of the lightened lock.

The greater the value of $\Delta E^*ab$, the greater the variation in coloration between the untreated locks and the lightened locks; and thus the more efficient the lightening.

The following results were obtained:

| | L* | a* | b* | $\Delta E^*ab$ |
|---|---|---|---|---|
| Untreated chestnut-brown hair | 18.2 | 1.8 | 1.3 | — |
| Hair treated with the inventive mixture (composition B1) | 22.1 | 6.3 | 7.3 | 8.5 |
| Hair treated with the comparative mixture (composition B2) | 21.6 | 5.2 | 5.2 | 6.2 |

The lightening obtained with composition B1 (inventive) was superior to that of composition B2 (comparative).

What is claimed is:

1. A process for dyeing or lightening human keratin fibers, comprising applying to the keratin fibers a composition comprising:
    a) at least one anhydrous composition (A) comprising at least one fatty substance and at least one surfactant;
    b) at least one composition (B) comprising monoethanolamine and at least one basic amino acid; and
    c) at least one composition (C) comprising at least one oxidizing agent;
    provided that when the process is a dyeing process, the at least one anhydrous composition (A) is free from organic amines and the at least one composition (B) comprises at least one oxidation dye and/or at least one direct dye.

2. The process according to claim 1, wherein the at least one fatty substance is chosen from $C_6$-$C_{16}$ lower alkanes, non-silicone oils of plant, mineral and/or synthetic origin, fatty alcohols, esters of a fatty acid and/or of a fatty alcohol, and silicones.

3. The process according to claim 1, wherein the at least one fatty substance is present in an amount ranging from 10% to 99% by weight, relative to the weight of the at least one anhydrous composition (A).

4. The process according to claim 3, wherein the at least one fatty substance is present in an amount ranging from 20% to 90% by weight, relative to the weight of the at least one anhydrous composition (A).

5. The process according to claim 4, wherein the at least one fatty substance is present in an amount ranging from 25% to 80% by weight, relative to the weight of the at least one anhydrous composition (A).

6. The process according to claim 1, wherein the at least one surfactant is at least one nonionic surfactant chosen from monooxyalkylenated, polyoxyalkylenated, monoglycerolated and polyglycerolated nonionic surfactants.

7. The process according to claim 1, wherein the at least one surfactant is present in an amount ranging from 0.1% to 50% by weight, relative to the weight of the at least one anhydrous composition (A).

8. The process according to claim 7, wherein the at least one surfactant is present in an amount ranging from 0.5% to 30% by weight, relative to the weight of the at least one anhydrous composition (A).

9. The process according to claim 1, wherein the at least one basic amino acid is chosen from the compounds of formula (I):

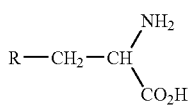

(I)

wherein R denotes a group chosen from:

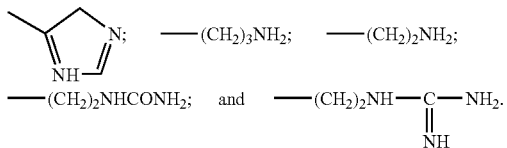

10. The process according to claim 9, wherein the at least one basic amino acid is chosen from arginine, histidine, and lysine.

11. The process according to claim 1, wherein the monoethanolamine is present in an amount ranging from 0.1% to 40% by weight, relative to the weight of the at least one composition (B).

12. The process according to claim 11, wherein the monoethanolamine is present in an amount ranging from 0.5% to 20% by weight, relative to the weight of the at least one composition (B).

13. The process according to claim 1, wherein the at least one basic amino acid is present in an amount ranging from 0.1% to 40% by weight, relative to the weight of the at least one composition (B).

14. The process according to claim 13, wherein the at least one basic amino acid is present in an amount ranging from 0.5% to 20% by weight, relative to the weight of the at least one composition (B).

15. The process according to claim 1, wherein the weight ratio of the monoethanolamine and the at least one basic amino acid present in the at least one composition (B) has a value ranging from 0.1 to 10.

16. The process according to claim 15, wherein the weight ratio of the monoethanolamine and the at least one basic amino acid present in the at least one composition (B) has a value ranging from 0.3 to 10.

17. The process according to claim 16, wherein the weight ratio of the monoethanolamine and the at least one basic amino acid present in the at least one composition (B) has a value ranging from 1 to 5.

18. The process according to claim 1, wherein applying to the keratin fibers comprises:
    mixing, at the time of use, the at least one anhydrous composition (A), the at least one composition (B), and the at least one composition (C); and
    applying the resultant composition to the keratin fibers.

19. The process according to claim 1, wherein the at least one anhydrous composition (A), the at least one composition (B), and the at least one composition (C) are applied to the keratin fibers, successively and without intermediate rinsing.

20. The process according to claim 1, wherein the at least one composition (B), the at least one anhydrous composition (A), and the at least one composition (C) are applied to the keratin fibers, successively and without intermediate rinsing.

21. The process according to claim 1, wherein applying to the keratin fibers comprises:
    applying to the keratin fibers the at least one composition (C);
    mixing, at the time of use, the at least one anhydrous composition (A) and the at least one composition (B) to form a resultant mixture, and
    applying the resultant mixture to the keratin fibers;
    wherein the at least one composition (C) and the resultant mixture are applied to the keratin fibers, successively and without intermediate rinsing.

22. The process according to claim 1, wherein the weight ratios R1 of the amounts of compositions [(A)+(B)]/(C) and R2 of the amounts of compositions (A)/(B) have a value ranging from 0.1 to 10.

23. The process according to claim 14, wherein the weight ratios R1 of the amounts of compositions [(A)+(B)]/(C) and R2 of the amounts of compositions (A)/(B) have a value ranging from 0.3 to 3.

24. A multi-compartment device comprising:
    a first compartment comprising at least one an anhydrous composition (A) comprising at least one fatty substance and at least one surfactant;
    a second compartment comprising at least composition (B) comprising monoethanolamine and at least one basic amino acid; and
    a third compartment comprising at least one composition (C) comprising at least one oxidizing agent.

* * * * *